(12) United States Patent
Jacobson et al.

(10) Patent No.: US 10,285,804 B2
(45) Date of Patent: *May 14, 2019

(54) SCLERAL PROSTHESIS FOR TREATING PRESBYOPIA AND OTHER EYE DISORDERS AND RELATED DEVICES AND METHODS

(71) Applicant: Refocus Group, Inc., Dallas, TX (US)

(72) Inventors: Harry R. A. Jacobson, Nashville, TN (US); Jack C. Griffis, III, Decatur, GA (US); Mark A. Cox, Dallas, TX (US); Douglas C. Williamson, Coppell, TX (US); Gene W. Zdenek, Northridge, CA (US); Peter J. Richardson, Buckinghamshire (GB); Michael K. Smolek, Pearl River, LA (US); Barrie D. Soloway, Long Beach, NY (US); Rex O. Bare, Lake Forest, GA (US); Andrew J. Scherer, Trabuco Canyon, CA (US); Timothy J. Payne, Santa Ana, CA (US)

(73) Assignee: Refocus Group, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,285

(22) Filed: Jun. 29, 2017

(65) Prior Publication Data

US 2017/0296329 A1    Oct. 19, 2017

Related U.S. Application Data

(63) Continuation of application No. 15/331,793, filed on Oct. 21, 2016, now Pat. No. 9,717,588, which is a
(Continued)

(51) Int. Cl.
*A61F 2/14*     (2006.01)
*A61F 2/16*     (2006.01)
(Continued)

(52) U.S. Cl.
CPC .......... *A61F 2/1624* (2013.01); *A61B 17/083* (2013.01); *A61F 2/14* (2013.01);
(Continued)

(58) Field of Classification Search
USPC .............................................. 623/4.1; 604/8
See application file for complete search history.

(56) References Cited

U.S. PATENT DOCUMENTS 2,952,023 A    9/1960    Rosen
3,064,643 A    11/1962   Dixon
(Continued)

FOREIGN PATENT DOCUMENTS

CN    1043257     6/1990
DE    42 32 021   4/1994
(Continued)

OTHER PUBLICATIONS

"Drug and Gene Delivery to the Back of the Eye: From Bench to Bedside", ARVO Eye Research Conference 2012, Jun. 15-16, 2012, 43 pages.
(Continued)

*Primary Examiner* — David H Willse
*Assistant Examiner* — Javier G Blanco

(57) ABSTRACT

A scleral prosthesis includes an elongated body having a first free end and a second free end opposite the first free end. A maximum width of the body at each end is wider than a maximum width of the body between the ends. The body includes multiple first portions that form the first free end of the body and a part of the body between the ends. The first portions are separated lengthwise along a substantial portion of a total length of the body. The first portions of the body are biased so that they maintain separation from one another without external interference but are configured to be pushed towards each other. The body is configured to receive and retain, between the first portions of the body, an insert that is configured to maintain the separation of the first portions.

20 Claims, 20 Drawing Sheets

Related U.S. Application Data continuation of application No. 14/975,152, filed on Dec. 18, 2015, now Pat. No. 9,504,559, which is a continuation of application No. 14/570,630, filed on Dec. 15, 2014, now Pat. No. 9,486,310, which is a continuation of application No. 13/654,249, filed on Oct. 17, 2012, now Pat. No. 8,911,496, which is a continuation-in-part of application No. 11/827,382, filed on Jul. 11, 2007, now Pat. No. 8,409,277.

(60) Provisional application No. 60/819,995, filed on Jul. 11, 2006.

(51) Int. Cl.
*A61F 9/00* (2006.01)
*A61F 9/007* (2006.01)
*A61B 17/08* (2006.01)
*A61B 17/10* (2006.01)

(52) U.S. Cl.
CPC .............. *A61F 2/147* (2013.01); *A61F 2/148* (2013.01); *A61F 9/0017* (2013.01); *A61F 9/00781* (2013.01); *A61B 17/10* (2013.01); *A61F 2210/00* (2013.01); *A61F 2210/009* (2013.01); *A61F 2210/0023* (2013.01)

(56) References Cited

U.S. PATENT DOCUMENTS

| | | |
|---|---|---|
| 3,454,966 A | 7/1969 | Rosen |
| 3,884,236 A | 5/1975 | Krasnov |
| 3,996,935 A | 12/1976 | Banko |
| 4,014,335 A | 3/1977 | Arnold |
| 4,174,389 A | 11/1979 | Cope |
| 4,349,027 A | 9/1982 | DiFrancesco |
| 4,391,275 A | 7/1983 | Fankhauser et al. |
| 4,439,198 A | 3/1984 | Brightman, II et al. |
| 4,452,235 A | 6/1984 | Reynolds |
| 4,521,210 A | 6/1985 | Wong |
| 4,549,529 A | 10/1985 | White |
| 4,603,697 A | 8/1986 | Kamerling |
| 4,782,820 A | 11/1988 | Woods |
| 4,839,342 A | 6/1989 | Kaswan |
| 4,846,172 A | 7/1989 | Berlin |
| 4,852,566 A | 8/1989 | Callahan et al. |
| 4,863,457 A | 9/1989 | Lee |
| 4,907,586 A | 3/1990 | Bille et al. |
| 4,923,699 A | 5/1990 | Kaufman |
| 4,946,436 A | 8/1990 | Smith |
| 4,961,744 A | 10/1990 | Kilmer et al. |
| 4,966,452 A | 10/1990 | Shields et al. |
| 4,976,719 A | 12/1990 | Siepser |
| 5,009,660 A | 4/1991 | Clapham |
| 5,022,413 A | 6/1991 | Spina, Jr. et al. |
| 5,025,811 A | 6/1991 | Dobrogowski et al. |
| 5,098,443 A | 3/1992 | Parel et al. |
| 5,109,846 A | 5/1992 | Thomas |
| 5,146,933 A | 9/1992 | Boyd |
| 5,152,759 A | 10/1992 | Parel et al. |
| 5,152,760 A | 10/1992 | Latina |
| 5,163,419 A | 11/1992 | Goldman |
| 5,174,304 A | 12/1992 | Latina et al. |
| 5,181,922 A | 1/1993 | Blumenkanz et al. |
| 5,267,553 A | 12/1993 | Graether |
| 5,292,514 A | 3/1994 | Capecchi et al. |
| 5,300,114 A | 4/1994 | Gwon et al. |
| 5,300,144 A | 4/1994 | Adams |
| 5,312,394 A | 5/1994 | Beckman |
| 5,323,788 A | 6/1994 | Silvestrini et al. |
| 5,354,331 A | 10/1994 | Schachar |
| 5,370,607 A | 12/1994 | Memmen |
| 5,372,595 A | 12/1994 | Gaasterland et al. |
| 5,439,462 A | 8/1995 | Bille et al. |
| 5,443,505 A | 8/1995 | Wong et al. |
| 5,459,133 A | 10/1995 | Neufeld |
| 5,465,737 A | 11/1995 | Schachar |
| 5,472,436 A | 12/1995 | Fremstad |
| 5,476,511 A | 12/1995 | Gwon et al. |
| 5,488,050 A | 1/1996 | Neufeld |
| 5,489,299 A | 2/1996 | Schachar |
| 5,503,165 A | 4/1996 | Schachar |
| 5,520,631 A | 5/1996 | Nordquist et al. |
| 5,529,076 A | 6/1996 | Schachar |
| 5,558,630 A | 9/1996 | Fisher |
| RE35,390 E | 12/1996 | Smith |
| 5,693,092 A | 12/1997 | Silvestrini et al. |
| 5,697,923 A | 12/1997 | Poler |
| 5,707,643 A | 1/1998 | Ogura et al. |
| 5,722,952 A | 3/1998 | Schachar |
| 5,731,909 A | 3/1998 | Schachar |
| 5,743,274 A | 4/1998 | Peyman |
| 5,766,242 A | 6/1998 | Wong et al. |
| 5,772,675 A | 6/1998 | Hellenkamp |
| 5,774,274 A | 6/1998 | Schachar |
| 5,782,894 A | 7/1998 | Israel |
| 5,824,073 A | 10/1998 | Peyman |
| 5,824,086 A | 10/1998 | Silvestrini |
| RE35,974 E | 12/1998 | Davenport et al. |
| 5,846,256 A | 12/1998 | Mathis et al. |
| 5,855,604 A | 1/1999 | Lee |
| 5,879,319 A | 3/1999 | Pynson et al. |
| 5,888,243 A | 3/1999 | Silverstrini |
| 5,919,228 A | 7/1999 | Hennig |
| 5,944,752 A | 8/1999 | Silvestrini |
| 5,956,126 A | 9/1999 | Cody |
| 5,964,748 A | 10/1999 | Peyman |
| 6,007,578 A | 12/1999 | Schachar |
| 6,042,594 A | 3/2000 | Hellenkamp |
| 6,053,909 A | 4/2000 | Shadduck |
| 6,126,687 A | 10/2000 | Peyman |
| 6,164,282 A | 12/2000 | Gwon et al. |
| 6,171,337 B1 | 1/2001 | Galin |
| 6,197,056 B1 | 3/2001 | Schachar |
| 6,206,919 B1 | 3/2001 | Lee |
| 6,217,571 B1 | 4/2001 | Peyman |
| 6,235,046 B1 | 5/2001 | Gerdt |
| 6,254,594 B1 | 7/2001 | Berry |
| 6,254,597 B1 | 7/2001 | Rizoiu et al. |
| 6,258,082 B1 | 7/2001 | Lin |
| 6,263,879 B1 | 7/2001 | Lin |
| 6,280,468 B1 | 8/2001 | Schachar |
| 6,282,449 B1 | 8/2001 | Kamerling et al. |
| 6,291,466 B1 | 9/2001 | Gwon et al. |
| 6,299,640 B1 | 10/2001 | Schachar |
| 6,302,877 B1 | 10/2001 | Ruiz |
| 6,306,075 B1 | 10/2001 | Shadduck |
| 6,387,107 B1 | 5/2002 | Hellenkamp |
| 6,410,544 B1 | 6/2002 | Gwon et al. |
| 6,450,984 B1 | 9/2002 | Lynch et al. |
| 6,464,724 B1 | 10/2002 | Lynch et al. |
| 6,491,688 B1 | 12/2002 | Lin et al. |
| 6,494,910 B1 | 12/2002 | Ganem et al. |
| 6,510,600 B2 | 1/2003 | Yaron et al. |
| 6,511,508 B1 | 1/2003 | Shahinpoor et al. |
| 6,517,555 B1 | 2/2003 | Caro |
| 6,524,275 B1 | 2/2003 | Lynch et al. |
| 6,527,780 B1 | 3/2003 | Wallace et al. |
| 6,547,714 B1 | 4/2003 | Dailey |
| 6,626,858 B2 | 9/2003 | Lynch et al. |
| 6,669,685 B1 | 12/2003 | Rizoiu et al. |
| 6,673,111 B2 | 1/2004 | Baikoff |
| 6,679,855 B2 | 1/2004 | Horn et al. |
| 6,682,560 B1 | 1/2004 | Baikoff |
| 6,692,524 B2 | 2/2004 | Baikoff |
| 6,712,847 B2 | 3/2004 | Baikoff et al. |
| 6,719,750 B2 | 4/2004 | Varner et al. |
| 6,726,664 B2 | 4/2004 | Yaron et al. |
| 6,730,056 B1 | 5/2004 | Ghaem et al. |
| 6,745,775 B2 | 6/2004 | Lin |
| 6,764,511 B2 | 7/2004 | Zadno-Azizi et al. |
| 6,780,164 B2 | 8/2004 | Bergheim et al. |
| 6,783,544 B2 | 8/2004 | Lynch et al. |
| 6,824,540 B1 | 11/2004 | Lin |

(56) References Cited

U.S. PATENT DOCUMENTS

| | | |
|---|---|---|
| 6,827,699 B2 | 12/2004 | Lynch et al. |
| 6,827,700 B2 | 12/2004 | Lynch et al. |
| 6,843,787 B2 | 1/2005 | Ruiz |
| 6,863,667 B2 | 3/2005 | Webb et al. |
| 6,923,955 B2 | 8/2005 | Till et al. |
| 7,037,335 B2 | 5/2006 | Freeman et al. |
| 7,044,945 B2 | 5/2006 | Sand |
| 7,060,094 B2 | 6/2006 | Shahinpoor et al. |
| 7,090,696 B2 | 8/2006 | Shahinpoor et al. |
| 7,252,662 B2 | 8/2007 | McArdle et al. |
| 7,275,545 B2 | 10/2007 | Lin |
| 7,282,046 B2 | 10/2007 | Simon |
| 7,338,506 B2 | 3/2008 | Caro |
| 7,458,380 B2 | 12/2008 | Jones et al. |
| 7,461,658 B2 | 12/2008 | Jones et al. |
| 7,470,286 B2 | 12/2008 | Tyler |
| 7,628,809 B2 | 12/2009 | Tyler |
| 7,635,388 B1 | 12/2009 | Tyler |
| 7,665,467 B2 | 2/2010 | Jones et al. |
| 7,704,278 B2 | 4/2010 | Roberts et al. |
| 7,736,389 B1 | 6/2010 | Damiano |
| 7,753,916 B2 | 7/2010 | Weber et al. |
| 7,862,531 B2 | 1/2011 | Yaron et al. |
| 8,167,938 B1 | 5/2012 | Damiano |
| 8,409,277 B2 | 4/2013 | Griffis, III et al. |
| 8,911,496 B2 | 12/2014 | Jacobson et al. |
| 9,486,310 B2 | 11/2016 | Jacobson et al. |
| 9,504,559 B2 | 11/2016 | Jacobson et al. |
| 9,717,588 B2 | 8/2017 | Jacobson et al. |
| 2001/0029363 A1 | 10/2001 | Lin |
| 2002/0010509 A1 | 1/2002 | Schachar |
| 2002/0025311 A1 | 2/2002 | Till |
| 2002/0026239 A1 | 2/2002 | Schachar |
| 2002/0103481 A1 | 8/2002 | Webb et al. |
| 2002/0120285 A1 | 8/2002 | Schachar et al. |
| 2002/0123804 A1 | 9/2002 | Gwon et al. |
| 2002/0138139 A1 | 9/2002 | Till |
| 2002/0161365 A1 | 10/2002 | Martins |
| 2002/0173777 A1 | 11/2002 | Sand |
| 2003/0028228 A1 | 2/2003 | Sand |
| 2003/0033015 A1 | 2/2003 | Zhou et al. |
| 2003/0038920 A1 | 2/2003 | Lin |
| 2003/0105456 A1 | 6/2003 | Lin |
| 2003/0139737 A1 | 7/2003 | Lin |
| 2003/0220630 A1 | 11/2003 | Lin et al. |
| 2004/0002756 A1 | 1/2004 | Baikoff et al. |
| 2004/0015140 A1 | 1/2004 | Shields |
| 2004/0024453 A1 | 2/2004 | Castillejos |
| 2004/0030269 A1 | 2/2004 | Horn et al. |
| 2004/0054374 A1 | 3/2004 | Weber et al. |
| 2004/0068256 A1 | 4/2004 | Rizoiu et al. |
| 2004/0078009 A1 | 4/2004 | Lin |
| 2004/0078030 A1 | 4/2004 | Lin |
| 2004/0098124 A1 | 5/2004 | Freeman et al. |
| 2004/0098125 A1 | 5/2004 | Freeman et al. |
| 2004/0098126 A1 | 5/2004 | Freeman et al. |
| 2004/0193262 A1 | 9/2004 | Shadduck |
| 2004/0254641 A1 | 12/2004 | Waldock |
| 2004/0260341 A1 | 12/2004 | Hays |
| 2004/0260395 A1 | 12/2004 | Boxer Wachler |
| 2004/0267294 A1 | 12/2004 | Will |
| 2005/0043722 A1 | 2/2005 | Lin |
| 2005/0112113 A1 | 5/2005 | Till et al. |
| 2005/0177229 A1 | 8/2005 | Boxer Wachler |
| 2005/0181018 A1 | 8/2005 | Peyman |
| 2005/0197697 A1 | 9/2005 | Baikoff et al. |
| 2005/0205101 A1 | 9/2005 | Lin |
| 2005/0241653 A1 | 11/2005 | Van Heugten et al. |
| 2005/0279369 A1 | 12/2005 | Lin |
| 2005/0283233 A1 | 12/2005 | Schachar |
| 2006/0004386 A1 | 1/2006 | Caro |
| 2006/0004387 A1 | 1/2006 | Caro |
| 2006/0074487 A1 | 4/2006 | Gilg |
| 2006/0110429 A1 | 5/2006 | Reiff et al. |
| 2006/0116759 A1 | 6/2006 | Thornton et al. |
| 2006/0116760 A1 | 6/2006 | Thornton et al. |
| 2006/0129129 A1 | 6/2006 | Smith |
| 2006/0129141 A1 | 6/2006 | Lin |
| 2006/0182781 A1 | 8/2006 | Hughes et al. |
| 2006/0224146 A1 | 10/2006 | Lin |
| 2006/0241650 A1 | 10/2006 | Weber et al. |
| 2006/0241750 A1 | 10/2006 | Zdenek et al. |
| 2006/0253111 A1 | 11/2006 | Van Valen |
| 2006/0259021 A1 | 11/2006 | Lin |
| 2007/0005046 A1 | 1/2007 | Lin |
| 2007/0016176 A1 | 1/2007 | Boutoussov et al. |
| 2007/0027537 A1 | 2/2007 | Castillejos |
| 2007/0055220 A1 | 3/2007 | Lin et al. |
| 2007/0073324 A1 | 3/2007 | Baikoff |
| 2007/0088352 A1 | 4/2007 | Rosen |
| 2007/0106376 A1 | 5/2007 | Roberts et al. |
| 2007/0162116 A1 | 7/2007 | Baikoff |
| 2007/0173794 A1 | 7/2007 | Frey et al. |
| 2007/0178062 A1 | 8/2007 | Ravi et al. |
| 2007/0185475 A1 | 8/2007 | Frey et al. |
| 2007/0203478 A1 | 8/2007 | Herekar |
| 2007/0219632 A1 | 9/2007 | Castillejos |
| 2007/0235043 A1 | 10/2007 | Baikoff |
| 2007/0260306 A1 | 11/2007 | Waldock |
| 2007/0276481 A1 | 11/2007 | Renner et al. |
| 2007/0299430 A1 | 12/2007 | McArdle et al. |
| 2008/0033409 A1 | 2/2008 | Jones et al. |
| 2008/0065053 A1 | 3/2008 | Jones et al. |
| 2008/0065054 A1 | 3/2008 | Van Valen |
| 2008/0091266 A1 | 4/2008 | Griffis et al. |
| 2008/0097416 A1 | 4/2008 | Jones et al. |
| 2008/0097417 A1 | 4/2008 | Jones et al. |
| 2008/0097418 A1 | 4/2008 | Jones et al. |
| 2008/0107712 A1 | 5/2008 | Shiah et al. |
| 2008/0125676 A1 | 5/2008 | Valen |
| 2008/0125677 A1 | 5/2008 | Valen |
| 2008/0139990 A1 | 6/2008 | Till et al. |
| 2008/0177383 A1 | 7/2008 | Shahinpoor et al. |
| 2009/0018650 A1 | 1/2009 | Boxer Wachler |
| 2009/0062780 A1 | 3/2009 | Jones et al. |
| 2009/0099654 A1 | 4/2009 | Griffis et al. |
| 2009/0105817 A1 | 4/2009 | Bretthauer et al. |
| 2009/0118719 A1 | 5/2009 | Jones et al. |
| 2009/0306687 A1 | 12/2009 | Yen et al. |
| 2010/0049176 A1 | 2/2010 | Tyler |
| 2010/0113535 A1 | 5/2010 | Ravi et al. |
| 2013/0103143 A1 | 4/2013 | Jacobson et al. |
| 2015/0094805 A1 | 4/2015 | Jacobson et al. |
| 2016/0166377 A1 | 6/2016 | Jacobson et al. |
| 2017/0035559 A1 | 2/2017 | Jacobson et al. |

FOREIGN PATENT DOCUMENTS

| | | |
|---|---|---|
| EP | 0 083 494 | 7/1983 |
| EP | 0 262 893 | 4/1988 |
| EP | 0 336 065 | 10/1989 |
| EP | 1 099 432 | 5/2001 |
| EP | 1 525 860 | 4/2005 |
| EP | 1 545 399 | 6/2005 |
| EP | 1 604 697 | 12/2005 |
| FR | 2838955 | 4/2000 |
| FR | 2 784 287 | 10/2000 |
| FR | 2 791 552 | 10/2003 |
| GB | 1456746 | 11/1976 |
| JP | 2002-527142 | 8/2002 |
| JP | 2003-501140 | 1/2003 |
| SG | 65893 | 8/1993 |
| SU | 1538914 | 1/1990 |
| SU | 1597188 | 10/1990 |
| TW | 82609 | 11/1986 |
| TW | 128961 | 4/1995 |
| WO | WO 89/09034 | 10/1989 |
| WO | WO 91/14406 | 10/1991 |
| WO | WO 94/02084 | 2/1994 |
| WO | WO 94/03129 | 2/1994 |
| WO | WO 94/06381 | 3/1994 |
| WO | WO 94/06504 | 3/1994 |
| WO | WO 94/07424 | 4/1994 |
| WO | WO 94/18921 | 9/1994 |

(56) References Cited

FOREIGN PATENT DOCUMENTS

| | | |
|---|---|---|
| WO | WO 95/03755 | 2/1995 |
| WO | WO 95/15120 | 6/1995 |
| WO | WO 95/28984 | 11/1995 |
| WO | WO 96/40005 | 12/1996 |
| WO | WO 98/42409 | 10/1998 |
| WO | WO 99/17684 | 4/1999 |
| WO | WO 99/17691 | 4/1999 |
| WO | WO 99/30645 | 6/1999 |
| WO | WO 99/30656 | 6/1999 |
| WO | WO 00/21466 | 4/2000 |
| WO | WO 00/25703 | 5/2000 |
| WO | WO 00/40174 | 7/2000 |
| WO | WO 00/56255 | 9/2000 |
| WO | WO 00/59406 | 10/2000 |
| WO | WO 00/74600 | 12/2000 |
| WO | WO 01/17460 | 3/2001 |
| WO | WO 01/45607 | 6/2001 |
| WO | WO 01/45608 | 6/2001 |
| WO | WO 01/82815 | 11/2001 |
| WO | WO 03/009784 | 2/2003 |
| WO | WO 2004/028409 | 4/2004 |
| WO | WO 2005/070034 | 8/2005 |
| WO | WO 2006/014484 | 2/2006 |
| WO | WO 2006/025806 | 3/2006 |
| WO | WO 2006/057859 | 6/2006 |
| WO | WO 2007/020184 | 2/2007 |
| WO | WO 2007/051345 | 5/2007 |
| WO | WO 2008/090225 | 7/2008 |
| ZA | 98/4634 | 2/1999 |
| ZA | 98/9149 | 6/1999 |

OTHER PUBLICATIONS

Adler-Grinberg, "Quesioning Our Classical Understanding of Accommodation and Presbyopia," Am. J. Optometry & Physiological Optics, 63(7) 571-580 (1986).
Arons, "Lasik and PRK climincal results are hot topics at the RSIG and ISRS meetings," Ocular Surgery News, http://www.slackline.com/eve/osn/19901a/lasik/asp, Jan. 1, 1999.
Atchison, "Accommodation and Presbyopia," Ophthal Physiol. Opt. 15 (4):255-272 (1995).
Banuelos et al., "Expandable Silicone Implants for Scleral Buckling," Arch Ophthalmol, 89:500-502 (1973).
Bernatchez, et al., "Biocompatibility of a new semisolid bioerodable poly(orth ester) intended to the ocular delivery of 5-fluorouracil," J. Biomedical Materials Research, 28:1037-1046 (1994).
Billson, et al., "Resiting Molteno Implant Tubes," Ophthalmic Surgery and Lasers, 27:801-803 (1996).
Brockhurst, "Dystrophic Calcification of Silicone Scleral Buckling Implant Materials," Am. J. Ophthalmol, 115:524-529 (1993).
Brouillette, et al., "Long-term results of modified trabeculectomy with Supramid implant for neovascular glaucoma," Can. J. Ophthalmol, 22(5):254-256 (1987).
Cameron, et al., "Clinico-histophatholigic Correlation of a Successful Glaucoma Pump-shunt Iplant," Ophthalmology, 95:1189-1194 (1988).
Campbell, et al., "Fluctuations of Accommodation Under Steady Viewing Conditions," J. Physiol., 145:579-594 (1959).
Coleman, et al., "Clinical Experience with the Ahmed Glaucoma Valve Implant in Eyes with prior or Current Penetrating Keratoplasties," Am. J. Ophth., 123:54-61 (1997).
Coleman, et al., "Initial Clinical Experience with the Ahmed Glaucoma Implant," Am. J. Ophth. 120:23-31 (1995).
Colosi, et al., "Intrusion of Scleral Implant Associated with Conjunctival Epithelial ingrowth," Am. J. Ophthalmol, 83:504-507 (1997).
Coltair, et al., "Scleral pocket incision applied to insertion of the nut and bolt keratoprosthesis," J. Cataract Refract. Surg., 16:649-651 (1990).
Crucea, et al., "Artificial draininge devices in glaucoma" Optalmologia, 47(2):5-10, abstract only (1999).

Daniele, et al., "Gelatin as an Absorbable Implant in Scleral Buckling Procedured," Arch Ophthal, 80:115-119 (1968).
Elander, "Scleral Expansion Surgery does not restore accommodatino in human presbyopia," J. Refract. Surg., 15(5):604 (1999).
Ellis, "Surgical Conquest of presbyopia; Are There Implications for Cataract and Glaucoma," Refractive Surgery, 38-44 (1999).
El-Sayyad, "The Use of Releasable Sutures in Molteno Glaucoma Implants to Reduce Postoperative Hypotony," Ophthalmic Surgery, 22:82-84 (1991).
Girard, et al., "Scleral fixation of a subluxated posterior chamber intraocular lens," J. Cataract Refract. Surg., 14:326-327 (1988).
Glasser, et al., "Presbyopia and the Optical Changes in the Human Crystalline Lens with Age," Vision Res., 38:209-229 (1998).
Harry R.A. Jacobson, et al., "Scleral Prosthesis for Treating Presbyopia and Other Eye Disorders and Related Devices and Methods", U.S. Appl. No. 14/974,777, filed Dec. 18, 2015.
Harry R.A. Jacobson, et al., "Scleral Prosthesis for Treating Presbyopia and Other Eye Disorders and Related Devices and Methods", U.S. Appl. No. 14/975,205, filed Dec. 18, 2015.
Hashizoe, et al., "Implantable biodegradable polymeric device in the treatment of experimental proliferative viteoretinopathy," Curr. Eye Res., 14(6):473-477 (1995).
Hashizoe, et al., "Scleral plug of biodegradable polymers for controlled drug release in the vitreous," Arch. Ophthalmol., 112(10):1380-1384 (1994).
Hasty, et al., "Primate Trabeculectomies with 5-fluorouracil Collagen Implants," Am. J. Ophthalmol, 109:721-725 (1990).
Hilton, et al., "The Removal of Scleral Buckles," Arch Ophthalmol, 96:2061-2063 (1978).
Ho, et al., "The MAI hydrophilic implant for scleral buckling: a view," Ophthalmic Surg., (6):611-5 (1984).
Jacklin, et al., "Gelatin as an Absorbable Implant in Scleral Buckling Procedure," Arch. Ophthalmol, 79:286-289 (1968).
Jacob, et al., "Synthetic scleral reinforcement materials. II Collagen types in the fibrous capsure," J. Biomedical Materials Research, 32:181-186 (1966).
Kimura, et al., "A new Vitreal Drug Delivery System Using an Implantable Biodegradable Polymeric Device," Investigative Ophthalmol and Visual Science, 35:2815-2819 (1994).
King, et al., "Gelatin Implants in Scleral Buckling Procedures," Arch. Ophthalmol., 93:807-811 (1975).
Krupin, et al., "A Long Krupin-Denver Valve Implant Attached to a 180 Scleral Explant for Glaucoma Surgery," Ophthalmol, 95:1174-1180 (1988).
Krupin, et al., "Filtering Valve Implant Surgery for Eyes with Neovascular Glaucoma," Am. J. Ophthalmol, 89:338-343 (1980).
Krupin, et al., "Long-Term Results of Valve Implants in Filtering Surgery Eyes with Neovascular Glaucoma," Am. J. Ophthalmol, 95:775-782 (1983).
Lambert, et al., "A New Alloplastic Material for Opthalmic Surgery," Ophthalmic Surgery, 9:35-42 (1978).
Lambert, et al., "Wedge Implant Used as an Explant," Am. J. Ophthalmol., 101:488-489 (1986).
Law, et al., "Retinal Complications after Aqueous Shunt Surgical Procedures for Glaucoma," Arch Ophthalmol, 114:1473-1480 (1996).
Levit, et al., "Use of Ophthalmic Gelfilm in retinal Surgery," Ann. Ophthalmol, 1613-1616 (Dec. 1975).
Lincoff, et al., "The Changing Character of the Infected Scleral Implant," Arch. Ophthalmol, 84:421 et seq (1970).
Lipner, "A Closer Look at Scleral Surgery," Eyeworld (Sep. 13, 1999) http://www.eyeworld.org/sep99/999p34.asp.
Liu, et al., "Scleral Buckling with a Soft Xerogel Implant: II Experiments in Vivo," Ophthalmic Surgery, 10:52-56 (1979).
Lloyd, et al., "Initial Clinical Experience with Baeveldt Implant in Complicated Glaucomas," Ophthalmology, 101:650-640 (1994).
Luttrull, et al., "Initial Experience with Pneumatically Stented baerveldt implant modifiedfor Pars Plana Insertion in Complicated Glaucoma," Ophthalmology, 107:143-149 (2000).
Luttrull, et al., "Pars Plana Implant and Vitrectomy for Treatment of Neovascular Glaucoma," Retina, 15:379-387 (1995).
Marin, et al., "Long-term Complications of the MAI Hydrogel Intrascleral Buckling Implant," Arch. Ophthalmol, 110:86-88 (1992).

(56) References Cited

OTHER PUBLICATIONS

Matthews, et al., Scleral Expansion Surgery Does Not Restore Accommodation in Human Presbyopia, Ophthalmology, 106:873-877 (1999).

Melamed, et al., "Molteno Implant Surgery in Refractory Glaucoma," Survey of Ophthalmology, 34:441-448 (1990).

Minckler, et al., Clinical Experience with the Single-plate Molteno Implant in Complicated Glaucomas, Ophthalmology 95:1181-1188 (1988).

Miyamoto, et al., "Biodegradable Scleral Implant for Controlled Release of Flocanazole," Current Eye Research, 16:930-935 (1997).

Ocular Surgery News, "Presbyopia Reversible in Pilot Studies," Jul. 1, 1999; http://www.slackinc.com/eve/osn/199907a/presby.asp.

Omi, et al., "Modified Schochet Implant for Refractory Glaucoma," Ophthalmology 98:211-214 (1991).

Peiffer, et al., "Long-term Comparative Study of the Schochet and Joseph Glaucoma Tube Shunts in Monkeys," Ophthalmic Surgery, 21:55-59 (1990).

Pruett, "The Fishmouth Phenomenon," Ach. Ophthalmol, 95:1777-181 (1977).

Rabowsky, et al., "The Use of Bioerodeable Polymers and Daunarubicin in Glaucoma Filtration Surgery," Ophthalmology, 103:800-807 (1996).

Ray, et al., "Gelatin Implants in Scleral Buckling Procedures," Arch Ophthalmol, 93:799-802 (1975).

Refojo, "Polymers in Ophthalmic Surgery," J. Biomed. Mater. Res., 5:113-119 (1971).

Refojo, et al., "Experimental Scleral Buckling with a Soft Xerogel Implant," Ophthalmic Surgery, 9:43-50 (1978).

Riggs, et al., "Intraocular Silicone Prostheses in a Dog and a Horse with Corneal Lacerations," J. Am. Vet. Med. Assoc., 196:617-619 (1990).

Rohr, et al., "Surgical Correction of Presbyopia," J. Osteopathic College of Ophthalomology and Otohinolaryngology, 12:34-36 (2000).

Rubsamen, et al., "Prevention of Experimental Poliferative Vitreoretinopathy with a Biodegradable Intravitreal Implant for the Sustained Release of Fluoroacil," Arch. Ophthalmol, 112:407-413 (1994).

Sakamoto, et al., "Silicone Sponge Implant in Combination with Episcleral Implant for Retinal Surgery," Ophthalmic Surgery, 11:712-718 (1980).

Sarkies, et al., "Silicone Tube and Gutter in Advanced Glaucoma," Trans. Ophthalmol, Soc. U.K., 144:133-136 (1985).

Schachar, "Cause and Treatment of Presbyopia With a Method for Increasing the Amplitude of Accommodation," Ann Ophthalmol, 24: 445-452 (1992).

Schachar, "Histology of the Ciliary Muscle-Zonular Connections," Ann Ophthalmol 28:70-79 (1996).

Schachar, "Pathophysiology of Accommodation and Presbyopia," J. Florida M.A. 81:268-271 (1994).

Schachar, "Zonular Function: A New Hypothesis with Clinical Implications," Ann Ophthalmol 26: 36-38 (1994).

Schachar, et al., "A Physical Model Demonstrating Schachar's Hypothesis of Accommocation," Ann Ophthalmol 26:4-9 (1994).

Schachar, et al., "A Revolutionary Variable Focus Lens," Annals of Ophthalmology, 2811-18 (1996).

Schachar, et al., "Equatorial Diameter During Accommodation," American Physiological Society R670-R676 (1996).

Schachar, et al., "Mathematic Proof of Schachar's Hypothesis of Accommodation," Ann Ophthalmol, 25: 5-9 (1993).

Schachar, et al., "The Effect of Gravity on the Amplitude of Accommodation," Ann Ophthalmol 26: 65-70 (1994).

Schachar, et al., "The Mechanism of Accommodation and Presbyopia in the Primate," Ann Ophthalmol 27:58-67 (1995).

Schachar, et al., "The Mechanism of Ciliary Muscle Function," Ann Ophthalmol 27:126-132 (1995).

Schachar, et al., Experimental Support for Schachar's Hypothesis of Accommodation, Ann Ophthalmol 25: 404-409 (1993).

Schepens, et al., "Scleral Implants: An Historic Perspective," Survey of Ophthalmology, 35:447-453 (1991).

Sherwood, et al., "Surgery for Refractory Glaucoma," Arch. Ophthalmol, 105:562-569 (1987).

Sidoti, et al., "Aqueous Tube Shunt to a Pre-existing Episcleral Encircling Element in the Treatment of Complicated Glaucomas," Ophthalmol, 101:1036-1043 (1994).

Sidoti, et al., "Epithelial Ingrowth and Glaucoma Drainage Implants," Ophthalmol, 101:872-875 (1994).

Smith, et al., "Comparison of the Double-Plate Molteno Drainage Implant with the Schochet Procedure," Arch. Ophthalmol, 110:1246-1250 (1992).

Smith, et al., "One-year results of the intrascleral glaucoma implant," J Cataract Refract. Surg., 21:453-456 (1995).

Speigel, et al., "Anterior Chamber Tube Shunt to an Encircling Band (Schochet procedure) in the Treatment of Refractory Glaucoma," Ophthalmic Surgery, 12:804-807 (1992).

Spencer P. Thornton, "Anterior Ciliary Sclerotomy (ACS), a Procedure to Reverse Presbyopia", Surgery for Hyperopia and Presbyopia, 1997, pp. 33-36.

Strubble, et al., "In vitro low characteristics of the Amhed and self-constructed anterior chamber shunts," Am. J. Vet. Res., 58:1332-1337 (1997).

Susanna, "Modifications of the Molteno Implants and implant Procedure," Ophthalmic Surgery, 22:611-613 (1991).

Sveinsson, et al., "Trabeulectomy and gelatin implants," Acta Ophthalmologica, 70:645-650 (1992).

Szymanski, "Scleral free auto-implant plug with mitomycin as limitation of trepanosclerectomy flow in glaucoma filtering surgery," International Ophthalmology, 20:89-94 (1997).

Tanji, et al., "Fascia Lata patch Graft in Glaucoma Tube Surgery," Ophthalmology, 103:1309-1312 (1996).

Tawakol, et al., "Gore-Tex Soft Tissue Bands as Scleral Explants in Rabbits: a Preliminary Histologic Study," Ophthalmic Surgery, 20:199-201 (1989).

Watzke, "Scleral Patch Graft for Exposed Episcleral Implants," Arch Ophthalmol, 102:114-115 (1984).

Wilson, et al., "Aqueous Shunts—Molteni versus Schocket," Ophthalmology, 99:672-678 (1992).

Wilson, et al., "New hope for presbyopia: PMMA scleral bands show promise," Eyeworld, (1999); http://www.eyeworld.org/apr98/963.html.

Wilson-Holt, et al., "Hypertrophy flowing insertion of inferiorly sited double-plate Molteno tubes," Eye, (Pt. 5): 515-20 (1992).

Yee, et al., "Scleral Expansion: New Surgical Technique to Correct Presbyopia," Investigative Ophthalmology & Visual Science, vol. 30(4), 5 (1997).

Yoshizumi, "Erosion of Implants in Retinal Detachment Surgery," Annals of Ophthalmology, 87:430-434 (1983).

Yoshizumi, "Exposure of Intrascleral Implants," Ophthalmology, 87:1150-1154 (1980).

Annex to Form PCT/ISA/206 Communication Relating to the Results of the Partial International Search dated Apr. 10, 2008 in PCT Application No. PCT/US2007/015774.

Notification of Transmittal of the International Search Report and the Written Opinion of the International Searching Authority, or the Declaration dated Jan. 29, 2014 in connection with PCT Application No. PCT/US2013/065370.

Notification of Transmittal of the International Search Report and the Written Opinion of the International Searching Authority, or the Declaration dated Mar. 18, 2009 in connection with PCT Application No. PCT/US2007/015816.

Notification of Transmittal of the International Search Report and the Written Opinion of the International Searching Authority, or the Declaration dated Nov. 7, 2008 in connection with PCT Application No. PCT/US2007/015774.

European Search Report dated Jul. 18, 2008 in connection with European Patent Application No. 06 00 7630, 7 pages.

European Search Report dated May 7, 2012 in connection with European Patent Application No. EP 12 15 8541, 6 pages.

Office Action dated Apr. 15, 2008 in connection with Canadian Patent Application No. 2,274,260, 3 pages.

Office Action dated Nov. 10, 2015 in connection with Canadian Patent Application No. 2,908,298.

(56) References Cited

OTHER PUBLICATIONS

Office Action dated Apr. 13, 2012 in connection with Japanese Patent Application No. 2009-519506, 10 pages.
Non-Final Office Action dated Apr. 11, 2014 in connection with U.S. Appl. No. 13/654,249; 17 pages.
Non-Final Office Action dated Apr. 24, 2012 in connection with U.S. Appl. No. 11/827,382; 14 pages.
Non-Final Office Action dated Aug. 16, 2010 in connection with U.S. Appl. No. 11/827,382; 11 pages.
Non-Final Office Action dated Dec. 2, 2014 in connection with U.S. Appl. No. 14/133,453; 19 pages.
Office Action dated Apr. 9, 2012 in connection with U.S. Appl. No. 12/960,917.
Office Action dated Aug. 12, 2009 in connection with U.S. Appl. No. 11/137,085.
Office Action dated Jan. 8, 2009 in connection with U.S. Appl. No. 09/972,533.
Office Action dated Jun. 16, 2009 in connection with U.S. Appl. No. 09/972,533.
Final Office Action dated Aug. 13, 2012 in connection with U.S. Appl. No. 11/827,382; 12 pages.
Final Office Action dated Feb. 22, 2011 in connection with U.S. Appl. No. 11/827,382; 14 pages.
Final Office Action dated May 7, 2015 in connection with U.S. Appl. No. 14/133,453; 18 pages.

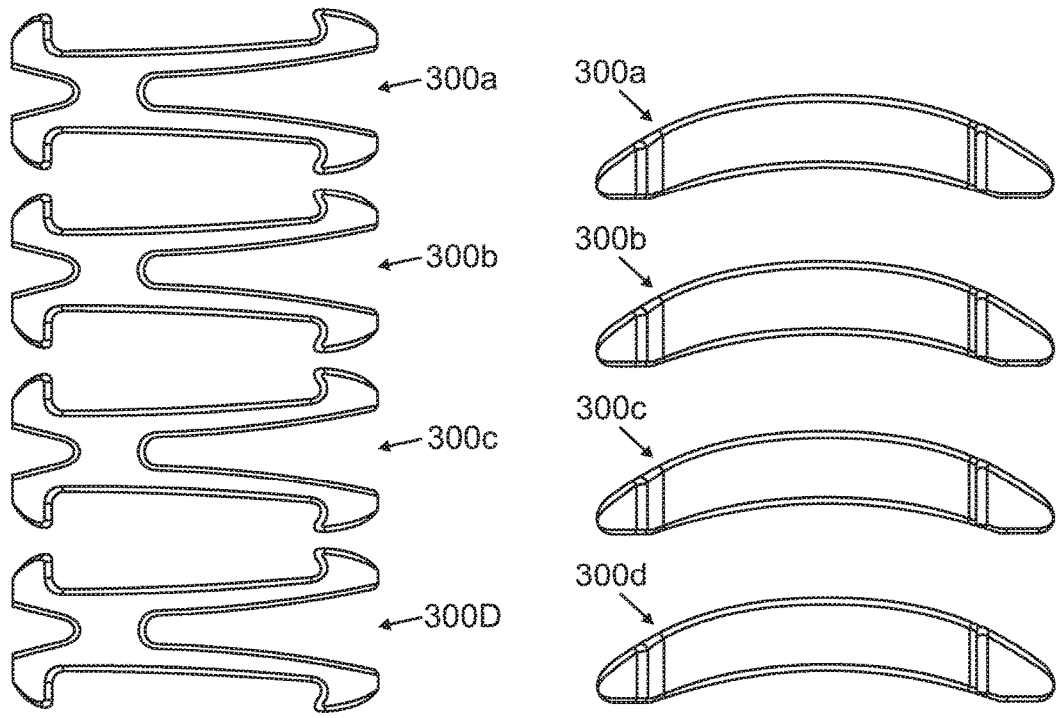
FIG. 3D  FIG. 3E
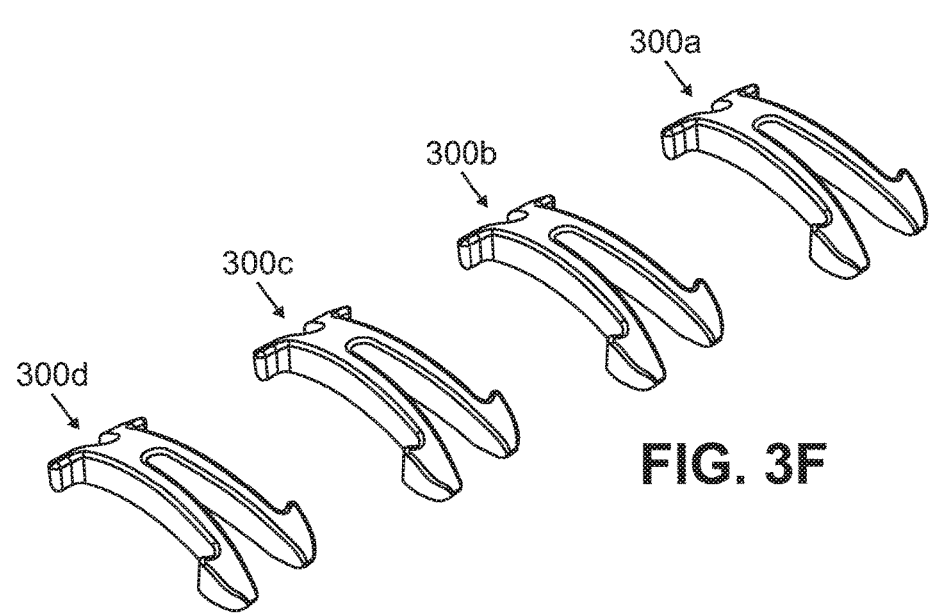
FIG. 3F

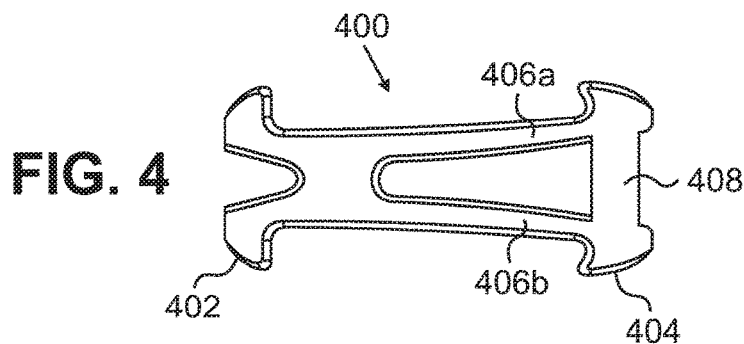
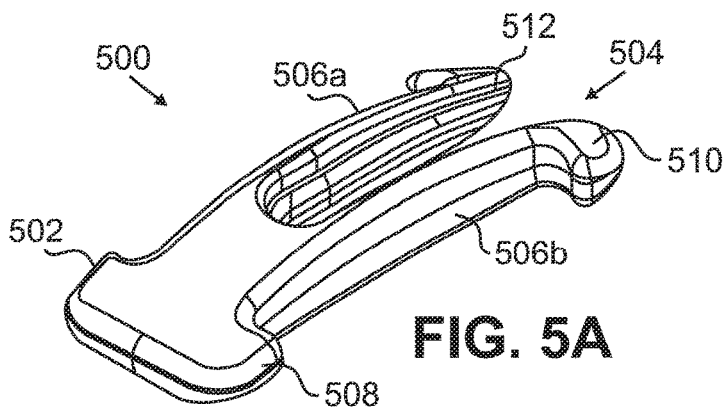
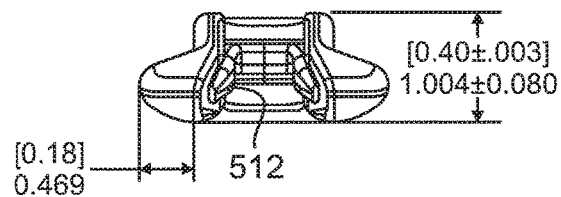
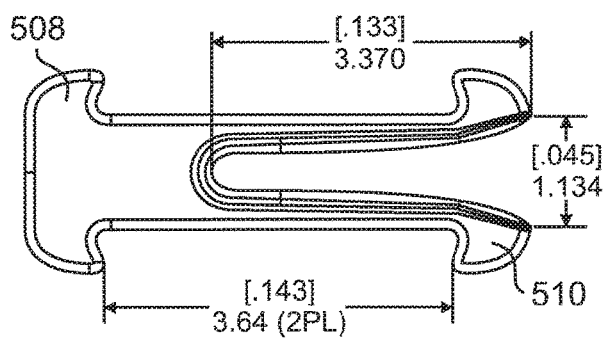

SCLERAL PROSTHESIS FOR TREATING PRESBYOPIA AND OTHER EYE DISORDERS AND RELATED DEVICES AND METHODS

CROSS-REFERENCE TO RELATED PATENT DOCUMENTS AND PRIORITY CLAIM

This application is a continuation of U.S. patent application Ser. No. 15/331,793 filed on Oct. 21, 2016 (now U.S. Pat. No. 9,717,588), which claims priority under 35 U.S.C. § 120 as a continuation of U.S. patent application Ser. No. 14/975,152 filed on Dec. 18, 2015 (now U.S. Pat. No. 9,504,559), which claims priority under 35 U.S.C. § 120 as a continuation of U.S. patent application Ser. No. 14/570,630 filed on Dec. 15, 2014 (now U.S. Pat. No. 9,486,310), which claims priority under 35 U.S.C. § 120 as a continuation of U.S. patent application Ser. No. 13/654,249 filed on Oct. 17, 2012 (now U.S. Pat. No. 8,911,496), which claims priority under 35 U.S.C. § 120 as a continuation-in-part of U.S. patent application Ser. No. 11/827,382 filed on Jul. 11, 2007 (now U.S. Pat. No. 8,409,277), which claims priority to U.S. Provisional Patent Application No. 60/819,995 filed on Jul. 11, 2006. All of these applications are hereby incorporated by reference.

This application is related to the following U.S. patent applications and issued patents:
(1) U.S. Pat. No. 6,007,578 entitled "Scleral Prosthesis for Treatment of Presbyopia and Other Eye Disorders" issued on Dec. 28, 1999;
(2) U.S. Pat. No. 6,280,468 entitled "Scleral Prosthesis for Treatment of Presbyopia and Other Eye Disorders" issued on Aug. 28, 2001;
(3) U.S. Pat. No. 6,299,640 entitled "Scleral Prosthesis for Treatment of Presbyopia and Other Eye Disorders" issued on Oct. 9, 2001;
(4) U.S. Pat. No. 5,354,331 entitled "Treatment of Presbyopia and Other Eye Disorders" issued on Oct. 11, 1994;
(5) U.S. Pat. No. 5,465,737 entitled "Treatment of Presbyopia and Other Eye Disorders" issued on Nov. 14, 1995;
(6) U.S. Pat. No. 5,489,299 entitled "Treatment of Presbyopia and Other Eye Disorders" issued on Feb. 6, 1996;
(7) U.S. Pat. No. 5,503,165 entitled "Treatment of Presbyopia and Other Eye Disorders" issued on Apr. 2, 1996;
(8) U.S. Pat. No. 5,529,076 entitled "Treatment of Presbyopia and Other Eye Disorders" issued on Jun. 25, 1996;
(9) U.S. Pat. No. 5,722,952 entitled "Treatment of Presbyopia and Other Eye Disorders" issued on Mar. 3, 1998;
(10) U.S. Pat. No. 6,197,056 entitled "Segmented Scleral Band for Treatment of Presbyopia and Other Eye Disorders" issued on Mar. 6, 2001;
(11) U.S. Pat. No. 6,579,316 entitled "Segmented Scleral Band for Treatment of Presbyopia and Other Eye Disorders" issued on Jun. 17, 2003;
(12) U.S. Pat. No. 6,926,727 entitled "Surgical Blade for Use with a Surgical Tool for Making Incisions for Scleral Eye Implants" issued on Aug. 9, 2005;
(13) U.S. Pat. No, 6,991,650 entitled "Scleral Expansion Device Having Duck Bill" issued on Jan. 31, 2006;
(14) U.S. Pat. No. 7,189,248 entitled "System and Method for Making Incisions for Scleral Eye Implants" issued on Mar. 13, 2007;
(15) U.S. Pat. No, 7,909,780 entitled "System and Method for Determining a Position for a Scleral Pocket for a Scleral Prosthesis" issued on Mar. 22, 2011;
(16) U.S. Pat. No. 7,785,367 entitled "Scleral Prosthesis for Treatment of Presbyopia and Other Eye Disorders" issued on Aug. 31, 2010;
(17) U.S. patent application Ser. No. 11/199,591 entitled "Surgical Blade for Use with a Surgical Tool for Making Incisions for Scleral Eye Implants" filed on Aug. 8, 2005 (now U.S. Pat. No. 8,361,098);
(18) U.S. patent application Ser. No. 11/252,369 entitled "Scleral Expansion Device Having Duck Bill" filed on Oct. 17, 2005;
(19) U.S. patent application Ser. No. 11/323,283 entitled "Surgical Blade for Use with a Surgical Tool for Making Incisions for Scleral Eye Implants" filed on Dec. 30, 2005 (now U.S. Pat. No. 8,500,767);
(20) U.S. Pat. No. 7,824,423 entitled "System and Method for Making Incisions for Scleral Eye Implants" issued on Nov. 2, 2010;
(21) U.S. patent application Ser. No. 11/322,728 entitled "Segmented Scleral Band for Treatment of Presbyopia and Other Eye Disorders" filed on Dec. 30, 2005 (now U.S. Pat. No. 8,663,205); and
(22) U.S. patent application Ser. No. 11/323,752 entitled "Segmented Scleral Band for Treatment of Presbyopia and. Other Eye Disorders" filed on Dec. 30, 2005 (now U.S. Pat. No. 8,663,206).

All of these U.S. patents and patent applications are hereby incorporated by reference.

TECHNICAL FIELD

This disclosure is generally directed to eye implants and associated devices, and more specifically to a scleral prosthesis for treating presbyopia and other eye disorders and related devices and methods.

BACKGROUND

In order for the human eye to have clear vision of an object at different distances (especially near objects), the effective focal length of the eye's crystalline lens is adjusted to keep an image of the object focused as sharply as possible on the retina. This change in effective focal length is known as "accommodation" and is accomplished by varying the shape of the crystalline lens in the eye. Generally, in the unaccommodated emmetropic eye, the curvature of the lens is such that distant objects are sharply imaged on the retina. In the unaccommodated eye, near objects are not focused sharply on the retina because their images lie behind the retinal surface. In order to visualize a near object clearly, the curvature of the crystalline lens is increased, thereby increasing its refractive power and causing the image of the near object to fall on the retina.

The change in the shape of the crystalline lens is accomplished by the action of certain muscles and structures within the eyeball or the "globe" of the eye. The lens is located in the forward part of the eye immediately behind the pupil. It has the shape of a classical biconvex optical lens, meaning it has a generally circular cross section with two convex refracting surfaces. The lens is located generally on the optical axis of the eye, which is typically the straight line from the center of the cornea to the macula in the retina at the posterior portion of the globe. In the unaccommodated eye, the curvature of the posterior surface of the lens (the surface adjacent to the vitreous body) is somewhat greater than the curvature of the anterior surface.

The lens is closely surrounded by a membranous capsule that serves as an intermediate structure in the support and actuation of the lens. The lens and its capsule are suspended on the optical axis behind the pupil by a circular assembly of radially directed elastic fibers called "zonules." The zonules are attached at their inner ends to the lens capsule and at their outer ends to the ciliary body and indirectly to the ciliary muscle. The ciliary muscle is a muscular ring of tissue located just within the sclera, the outer supporting structure of the eye.

According to the classical theory of accommodation originating with Helmholtz, the ciliary muscle is relaxed in the unaccommodated eye and therefore assumes its largest diameter. The relatively large diameter of the ciliary muscle in this condition causes a tension on the zonules, which pull radially outward on the lens capsule. This causes the equatorial diameter of the lens to increase slightly and decreases the anterior-posterior dimension of the lens at the optical axis. In other words, the tension on the lens capsule causes the lens to assume a flattened state where the curvature of the anterior surface, and to some extent the posterior surface, is less than it would be in the absence of the tension. In this state, the refractive power of the lens is relatively low, and the eye is focused for clear vision on distant objects.

According to the classical theory, when the eye is intended to be focused on a near object, the ciliary muscle contracts. This contraction causes the ciliary muscle to move forward and inward, thereby relaxing the outward pull of the zonules on the equator of the lens capsule. This reduced zonular tension allows the elastic capsule of the lens to contract, causing an increase in the anterior-posterior dimension of the lens at the optical axis (meaning the lens becomes more spherical). This results in an increase in the optical power of the lens. Because of topographical differences in the thickness of the lens capsule, the central anterior radius of curvature may change more than the central posterior radius of curvature. This is the accommodated condition of the eye, where images of near objects fall sharply on the retina.

Presbyopia is the universal decrease in the amplitude of accommodation, which is typically observed in individuals over forty years of age. In a person having normal vision or "emmetropic" eyes, the ability to focus on near objects is gradually lost. As a result, the individual comes to need glasses for tasks requiring near vision, such as reading.

According to the conventional view, the amplitude of accommodation of the aging eye is decreased because of the loss of elasticity of the lens capsule and/or sclerosis of the lens with age. Consequently, even though the radial tension on the zonules is relaxed by contraction of the ciliary muscle, the lens does not assume a greater curvature. According to this conventional view, it is not possible to restore the accommodative power to the presbyopic eye by any treatment. The loss of elasticity of the lens and its capsule is seen as irreversible. One solution to the problems presented by presbyopia is to use corrective lenses for close work or possibly bifocal lenses if corrective lenses are required for distant vision. Other solutions may include surgically reshaping the cornea of the eye or implanting a presbyopic intra-ocular lens in the eye Contrary to the conventional view, it is possible to restore the accommodative power to a presbyopic eye by implanting scleral prostheses within the sclera of the eye. For each individual scleral prosthesis, an incision is made in the sclera of the eye, such as near the plane of the equator of the crystalline lens. The incision is then extended under the surface of the sclera to form a scleral "tunnel," and a scleral prosthesis is placed within the tunnel. A typical scleral prosthesis could be formed from a generally rectangular-shaped bar approximately five millimeters long, one and a half millimeters wide, and one millimeter tall. One or multiple scleral prostheses may be implanted in a patient's eye to partially or completely restore the accommodative power to a presbyopic eye. The same or similar technique can also be used to treat glaucoma, ocular hypertension, elevated intraocular pressure, or other eye disorders. This technique is described more fully in the U.S. patents and patent applications incorporated by reference above.

SUMMARY

This disclosure provides a scleral prosthesis for treating presbyopia and other eye disorders and related devices and methods.

In a first embodiment, a scleral prosthesis includes an elongated body having a first free end and a second free end opposite the first free end. A maximum width of the body at each end is wider than a maximum width of the body between the ends. The body includes multiple first portions that form the first free end of the body and a part of the body between the ends. The first portions are separated lengthwise along a substantial portion of a total length of the body. The first portions of the body are biased so that they maintain separation from one another without external interference but are configured to be pushed towards each other. The body is configured to receive and retain, between the first portions of the body, an insert that is configured to maintain the separation of the first portions.

In a second embodiment, a system includes a scleral prosthesis configured to be implanted into scleral tissue of an eye. The scleral prosthesis includes an elongated body having a first free end and a second free end opposite the first free end. A maximum width of the body at each end is wider than a maximum width of the body between the ends. The body includes multiple first portions that form the first free end of the body and a part of the body between the ends. The first portions are separated lengthwise along a substantial portion of a total length of the body. The first portions of the body are biased so that they maintain separation from one another without external interference but are configured to be pushed towards each other. The system also includes an insert configured to be placed between the first portions of the body to maintain a separation of the first portions.

In a third embodiment, a method includes forming an elongated body of a scleral prosthesis. The body has a first free end and a second free end opposite the first free end. A maximum width of the body at each end is wider than a maximum width of the body between the ends. The method also includes forming an insert for the body. The body includes multiple first portions that form the first free end of the body and a part of the body between the ends. The first portions are separated lengthwise along a substantial portion of a total length of the body. The first portions of the body are biased so that they maintain separation from one another without external interference but are configured to be pushed towards each other. The body is configured to receive and retain, between the first portions of the body, the insert to maintain the separation of the first portions.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which:

FIGS. 3A through 3F illustrate a third example scleral prosthesis in accordance with this disclosure;

FIG. 4 illustrates a fourth example scleral prosthesis in accordance with this disclosure;

FIGS. 5A through 5G illustrate a fifth example scleral prosthesis in accordance with this disclosure;

DETAILED DESCRIPTION

Figure 1A:
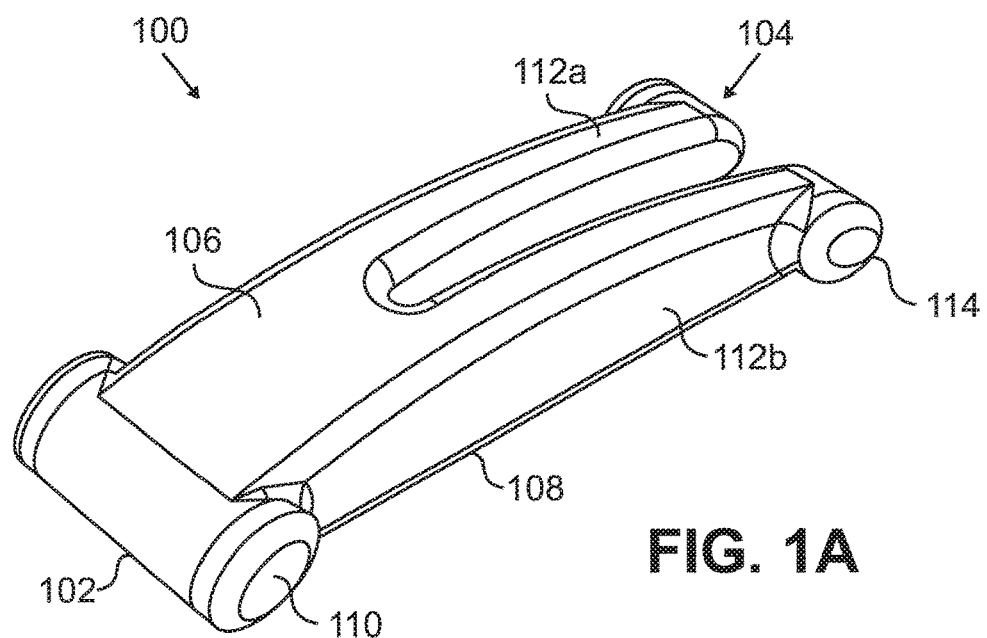
FIGS. 1A and 1B illustrate a first example scleral prosthesis in accordance with this disclosure.
Figure 1B:
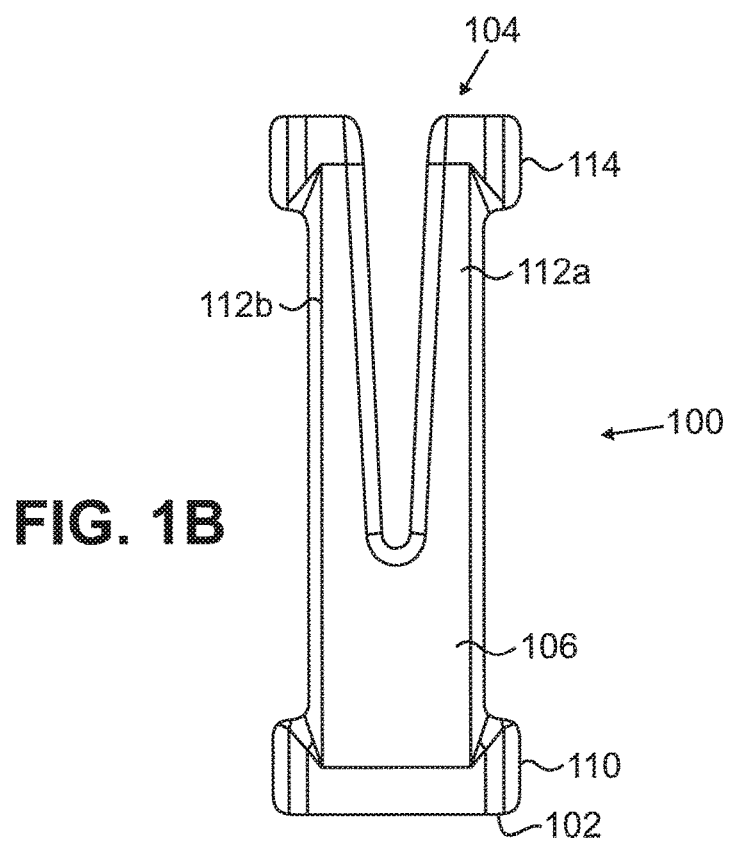

FIGS. 1A and 1B illustrate a first example scleral prosthesis 100 in accordance with this disclosure. The embodiment of the scleral prosthesis 100 shown in FIGS. 1A and 1B is for illustration only. Other embodiments of the scleral prosthesis 100 could be used without departing from the scope of this disclosure.

As shown in FIGS. 1A and 1B, the scleral prosthesis 100 has two opposing ends 102-104, a top surface 106, and a bottom surface 108. One end 102 of the prosthesis 100 includes a generally cylindrical area 110 with a flat bottom forming a base on which the prosthesis 100 sits. The other end 104 of the prosthesis 100 is divided or split into multiple portions 112a-112b. Each of these portions 112a-112b includes a generally cylindrical area 114 with a flat bottom, which collectively form another base on which the prosthesis 100 sits.

In this example, the portions 112a-112b of the prosthesis 100 span a majority of the length of the prosthesis 100, meaning the prosthesis 100 is split along at least half of its length (or some other substantial portion of its length). The portions 112a-112b are generally biased so that they remain separated from one another without external interference. The portions 112a-112b may be biased such that they can be pushed towards each other or together but then separate after release. Also, the portions 112a-112b may not be excessively biased to the point where they tear through an incision in the patient's eye or pull the prosthesis 100 out of a scleral tunnel. Also, the cylindrical areas 110 and 114 project out from the sides of the prosthesis 100, meaning the cylindrical areas 110 and 114 form bases that are wider than the middle portion of the prosthesis 100. In addition, in this example, the top surface 106 of the prosthesis 100 is generally curved, and the bottom surface 108 could be generally flat or curved.

In this example embodiment, the scleral prosthesis 100 can be implanted within a scleral tunnel in a patient's eye. For example, the scleral prosthesis 100 can be implanted such that the cylindrical areas 110 and 114 remain outside of the scleral tunnel. Also, the flat bottoms of the cylindrical areas 110 and 114 can lie on the surface of the patient's eye outside of the scleral tunnel. To implant the scleral prosthesis 100 in the scleral tunnel, the portions 112a-112b of the scleral prosthesis 100 could be pushed together and pulled through the scleral tunnel. This may help to reduce the width or cross-sectional area of the end 104 of the scleral prosthesis 100 as the prosthesis 100 is pulled through the scleral tunnel during implantation. However, any other suitable technique could be used to implant the scleral prosthesis 100 in a scleral tunnel.

The scleral tunnel in which the scleral prosthesis 100 is implanted can be formed near the ciliary body of a patient's eye. Once implanted in a scleral tunnel, the scleral prosthesis 100 helps to, for example, increase the amplitude of accommodation of the patient's eye. The scleral prosthesis 100 could also help to treat other eye conditions, such as glaucoma, ocular hypertension, elevated intraocular pressure, or other eye disorders. In some embodiments, multiple prostheses (such as four) are implanted in a patient's eye, and the ends of the prostheses are "free" (not attached to the ends of other prostheses).

By making the ends of the scleral prosthesis 100 wider than its middle portion, various benefits could be obtained, such as stabilization of the prosthesis 100. For example, with wider ends, it is less likely that the scleral prosthesis 100 would turn or rotate within a scleral tunnel after implantation. Also, the wider ends help to lock the scleral prosthesis 100 into place and impede movement of the scleral prosthesis 100. In addition, the wider ends make it less likely that the scleral prosthesis 100 can be inadvertently ejected out of the scleral tunnel after implantation.

In particular embodiments, the prosthesis 100 in FIGS. 1A and 1B may be formed from a single integrated piece of material, such as polymethyl methacrylate ("PMMA"), polyether-ether ketone ("PEEK"), or other suitable material(s). Also, the scleral prosthesis 100 could have any suitable size and dimensions, and scleral prostheses 100 of different sizes could be provided. For example, different-sized scleral prostheses 100 could have different lengths, such as lengths of 3.6, 3.8, 4.0, and 4.2 millimeters from the inner edges of the cylindrical areas 110 and 114 of the prostheses 100.

Figure 2A:
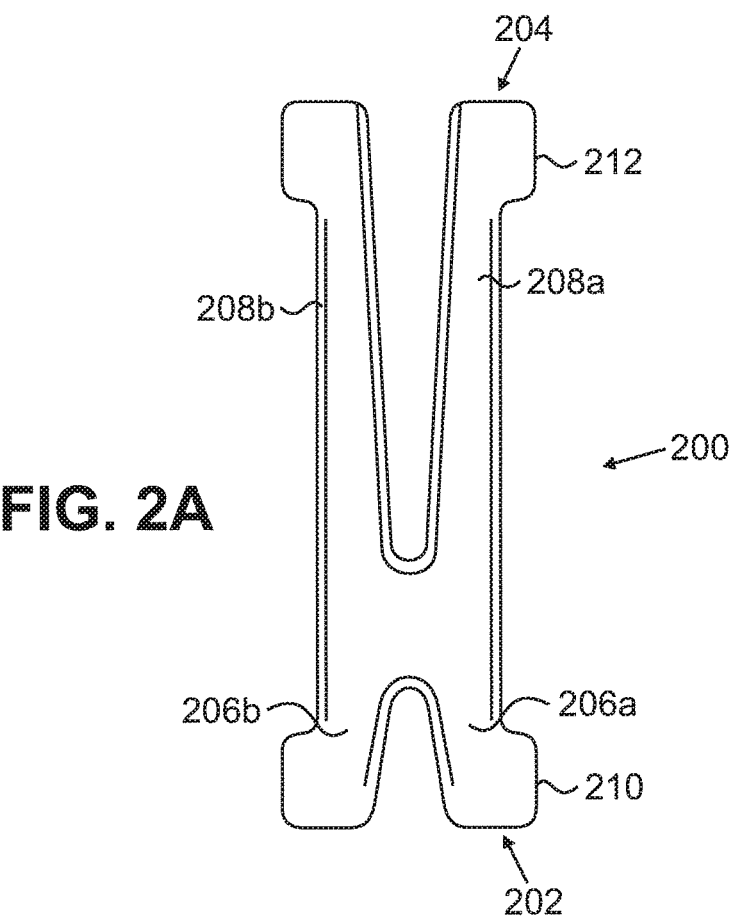
FIGS. 2A and 2B illustrate a second example scleral prosthesis in accordance with this disclosure.
Figure 2B:
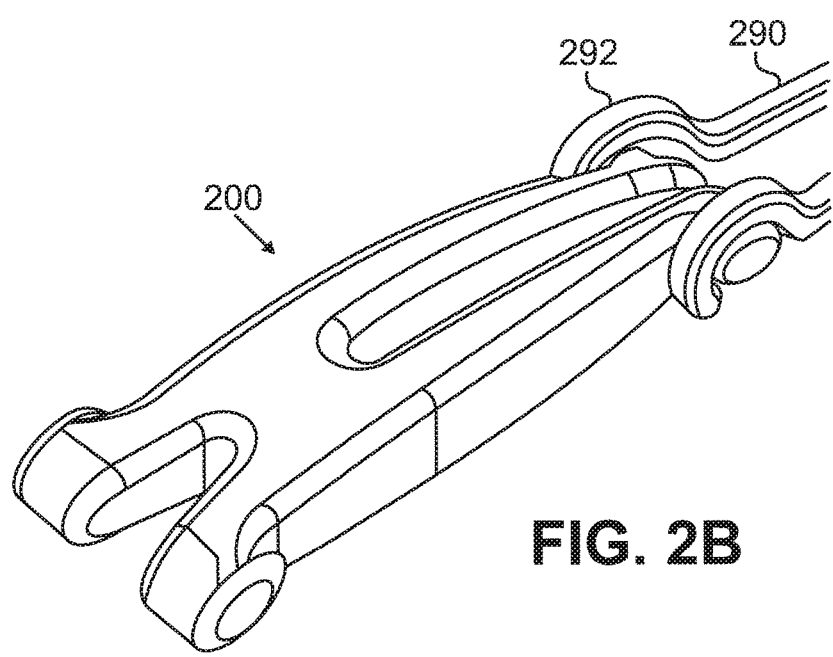

FIGS. 2A and 2B illustrate a second example scleral prosthesis 200 in accordance with this disclosure. The embodiment of the scleral prosthesis 200 shown in FIGS. 2A and 2B is for illustration only. Other embodiments of the scleral prosthesis 200 could be used without departing from the scope of this disclosure.

The scleral prosthesis 200 in FIGS. 2A and 2B is similar to the scleral prosthesis 100 of FIGS. 1A and 1B. In this example embodiment, the scleral prosthesis 200 includes opposing ends 202-204. In this example, both ends 202-204 are split or divided into multiple portions 206a-206b and 208a-208b, respectively. Each of these end portions 206a-

206*b* and 208*a*-208*b* includes a generally cylindrical area 210 or 212, which could have flat bottoms collectively define two bases for the scleral prosthesis 200.

In this example embodiment, the scleral prosthesis 200 can be implanted within a scleral tunnel in a patient's eye, such as by implanting the scleral prosthesis 200 so that the cylindrical areas 210 and 212 remain outside of the scleral tunnel. Also, the flat bottom portions of the cylindrical areas 210 and 212 can lie on the surface of the patient's eye outside of the scleral tunnel. Further, the cylindrical areas 210 and 212 project out from the sides of the prosthesis 200, forming bases that are wider than the middle portion of the prosthesis 200. As noted above, this may help to stabilize the scleral prosthesis 200, such as by reducing or preventing rotation, locking the prosthesis 200 into place, impeding movement of the prosthesis 200, and reducing the likelihood that the prosthesis 200 can exit the scleral tunnel. In addition, in this example, the top surface of the prosthesis 200 is generally curved, and the bottom surface could be generally flat or curved.

To implant the scleral prosthesis 200 in the scleral tunnel, the portions 206*a*-206*b* or 208*a*-208*b* of the scleral prosthesis 200 can be pushed together and pulled through the scleral tunnel. An example of this is shown in FIG. 2B. Here, a tool 290 has two hooked ends 292 that can hook around or onto the cylindrical areas 212 of the scleral prosthesis 200. The tool 290 is then used to push the split portions 208*a*-208*b* of the scleral prosthesis 200 together, and the prosthesis 200 can be pulled into the scleral tunnel. However, any other suitable technique could be used to implant the scleral prosthesis 200 in a scleral tunnel.

In particular embodiments, the prosthesis 200 in FIGS. 2A and 2B may be formed from a single integrated piece of material, such as PMMA, PEEK, or other suitable material(s). The scleral prosthesis 200 could also have any suitable size and dimensions, and scleral prostheses 200 of different sizes could be provided.

FIGS. 3A through 3F illustrate a third example scleral prosthesis 300 in accordance with this disclosure. The embodiment of the scleral prosthesis 300 shown in FIGS. 3A through 3F is for illustration only. Other embodiments of the scleral prosthesis 300 could be used without departing from the scope of this disclosure.

Figure 3A:
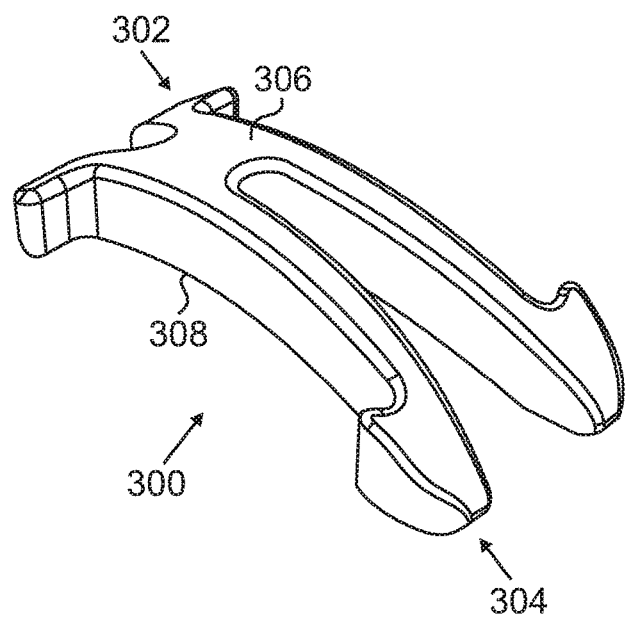
Figure 3B:
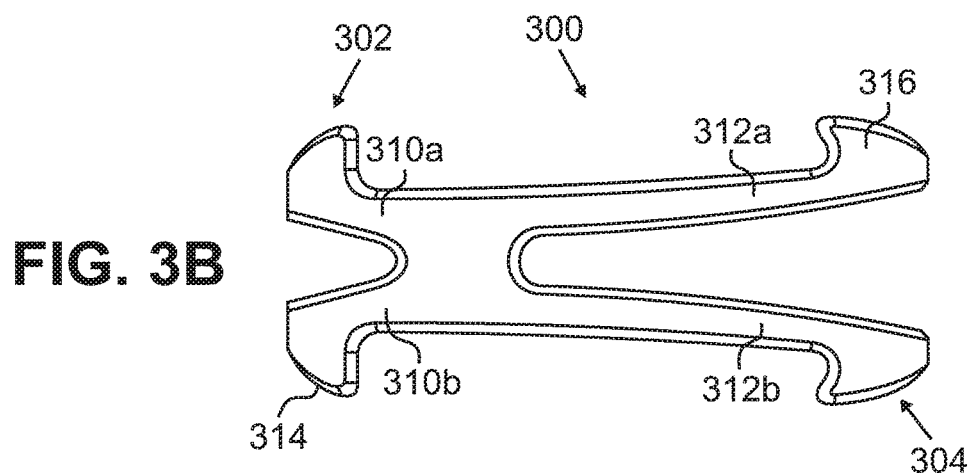
Figure 3C:
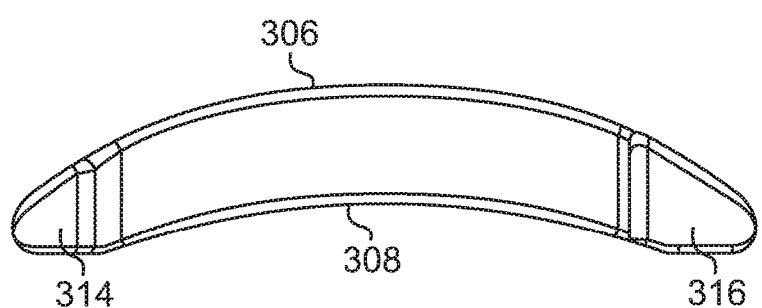

As shown in FIGS. 3A through 3C, the scleral prosthesis 300 has two opposing ends 302-304, a top surface 306, and a bottom surface 308. One end 302 of the prosthesis 300 is split or divided into multiple portions 310*a*-310*b*, and the other end 304 of the prosthesis 300 is split or divided into multiple portions 312*a*-312*b*.

In this example, the portions 310*a*-310*b* of the prosthesis 300 span less than a quarter of the length of the prosthesis 300 (or some other less substantial portion of its length), and the portions 312*a*-312*b* of the prosthesis 300 span more than half of the length of the prosthesis 300 (or some other more substantial portion of its length). Also, in this example, the ends 302-304 of the prosthesis 300 have areas 314-316, respectively, that are more triangular in shape. As shown in FIG. 3B, the areas 314 at the end 302 of the scleral prosthesis 300 have surfaces that generally face the opposing end 304. Also, as shown in FIG. 3B, the areas 316 at the end 304 of the scleral prosthesis 300 have surfaces that are hook-shaped (the areas 316 hook back towards the opposing end 302 of the scleral prosthesis 300). These areas 314 and 316 may also include generally flat bottom surfaces that form bases for the prosthesis 300.

In this example embodiment, the scleral prosthesis 300 can be implanted within a scleral tunnel in a patient's eye, such as by implanting the scleral prosthesis 300 so that the areas 314 and 316 remain outside of the scleral tunnel. Also, the flat bottom portions of the areas 314 and 316 can lie on the surface of the patient's eye outside of the scleral tunnel. Further, the areas 314 and 316 project out from the sides of the prosthesis 300 to form bases wider than the middle portion of the prosthesis 300. Again, the wider ends may provide certain benefits for the scleral prosthesis 300, such as stabilization of the prosthesis 300. In addition, in this example, the top surface 306 and the bottom surface 308 of the prosthesis 300 are generally curved.

In particular embodiments, the prosthesis 300 in FIGS. 3A through 3C may be formed from a single integrated piece of material, such as PMMA, PEEK, or other suitable material(s). Also, the scleral prosthesis 300 could have any suitable size and dimensions, and scleral prostheses 300 of different sizes could be provided.

Examples of differently sized and dimensioned prostheses are shown in FIGS. 3D through 3F, which illustrate four different prostheses 300*a*-300*d*. The prostheses 300*a*-300*d* are similar to one another with slight changes in their structure. For example, the prosthesis 300*a* has a larger arch and flat bottom surfaces at its ends, while the prosthesis 300*c* has a smaller arch and flat bottom surfaces at its ends. The prosthesis 300*b* has a larger arch and slanted bottom surfaces at its ends, while the prosthesis 300*d* has a smaller arch and slanted bottom surfaces at its ends.

The prostheses 300*a*-300*d* in FIGS. 3D through 3F could have any suitable sizes and dimensions. For example, the prostheses 300*a*-300*d* could be 5,366 microns in length. A thickness (measured top-to-bottom) at the middle (measured end-to-end) of the prostheses 300*a*-300*d* could have various values, such as 831, 833, and 839 microns, The arch (measured from the tips of the prostheses to the top of the arch) of the prostheses 300*a*-300*d* could also have various values, such as 212, 311, and 386 microns.

FIG. 4 illustrates a fourth example scleral prosthesis 400 in accordance with this disclosure. The embodiment of the scleral prosthesis 400 shown in FIG. 4 is for illustration only. Other embodiments of the scleral prosthesis 400 could be used without departing from the scope of this disclosure.

In this example, the scleral prosthesis 400 in FIG. 4 is similar to the prosthesis 300 shown in FIGS. 3A through 3C. Here, the scleral prosthesis 400 includes two opposing ends 402-404, where the end 404 is split or divided into multiple portions 406*a*-406*b*.

The prosthesis 400 also includes an insert 408 placed between or around the multiple portions 406*a*-406*b* of the end 404 of the prosthesis 400. The insert 408 can be permanently or removably placed between or around the portions 406*a*-406*b* of the end 404 of the prosthesis 400. For example, the insert 408 could be placed between or around the portions 406*a*-406*b* of the end 404 after the prosthesis 400 has been implanted in a scleral tunnel in a patient's eye. The insert 408 could later be removed, such as to facilitate removal of the prosthesis 400 from the scleral tunnel.

The insert 408 may generally help to stabilize the prosthesis 400 (in addition to the stabilization already provided by the wider ends). For example, the insert 408 could help to prevent the portions 406*a*-406*b* of the prosthesis 400 from separating excessively, which could pull the opposite end 402 through the scleral tunnel and force the prosthesis 400 out of the tunnel completely. The insert 408 could also function to reduce or prevent rotation of the prosthesis 400 within the scleral tunnel. For instance, the insert 408 may help to ensure that the end 404 of the prosthesis 400 maintains a desired width and therefore remains wide enough to prevent the prosthesis 400 from rolling over once implanted in the scleral tunnel. Moreover, the insert 408 can be inserted into or around the prosthesis 400 only after the prosthesis 400 has been implanted, which enables the portions 406a-406b of the prosthesis 400 to be pushed together during implantation while preventing portions 406a-406b from coming together after implantation (reducing the likelihood that the prosthesis 400 can exit the scleral tunnel).

The insert 408 could be attached or coupled to the prosthesis 400 in any suitable manner. For example, the insert 408 could have one or more structures that engage one or more corresponding structures of the portions 406a-406b of the prosthesis 400, such as male structures on the insert 408 that engage female structures on the prosthesis body. The insert 408 could also be attached to the prosthesis 400 using sutures or looped around the prosthesis 400. The insert 408 could be attached or coupled to the prosthesis 400 in any other suitable manner.

FIGS. 5A through 5G illustrate a fifth example scleral prosthesis 500 in accordance with this disclosure. The embodiment of the scleral prosthesis 500 shown in FIGS. 5A through 5G is for illustration only. Other embodiments of the scleral prosthesis 500 could be used without departing from the scope of this disclosure.

As shown in FIG. 5A, the scleral prosthesis 500 has two opposing ends 502-504. In this example, only one end 504 of the prosthesis 500 is split or divided into multiple portions 506a-506b (although both could be). As shown in FIG. 5B, the ends of the prosthesis 500 generally have an oval cross-section. Except for the more oval cross-section and the undivided end 502, the overall shape of the prosthesis 500 is similar to the shape of the prosthesis 300.

As shown here, portions 508-510 of the ends 502-504 of the prosthesis 500 are hook-shaped, where the portions 508 of the end 502 are hooked back towards the end 504 and the portions 510 of the end 504 are hooked back towards the end 502. These portions 508-510 of the prosthesis 500 could also lie outside of a scleral tunnel and rest on the surface of a patient's eye. Again, the ends 502-504 of the prosthesis 500 are wider than the middle, helping to stabilize the prosthesis 500.

In this example, the prosthesis 500 also includes ridges 512 along the inner sides of the portions 506a-506b The ridges 512 generally travel lengthwise along the portions 506a-506b of the prosthesis 500. The ridges 512 may or may not link up to each other along the curved intersection of the portions 506a-506b. The ridges 512 may have any suitable height, width, or shape.

Figure 5D:
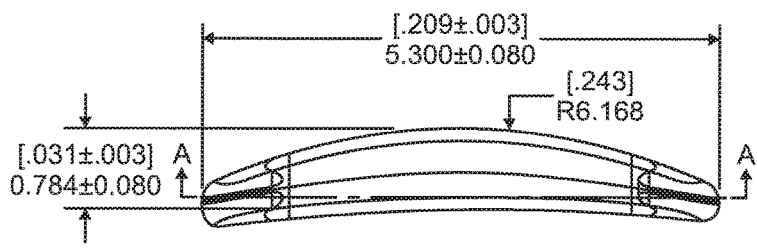
Figure 5E:
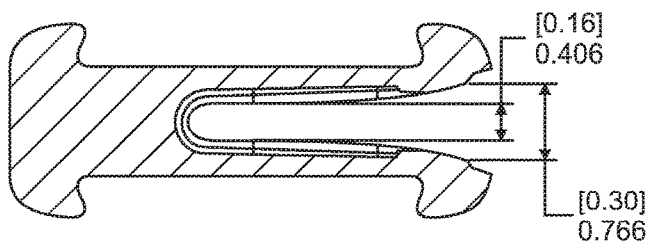
Figure 5F:
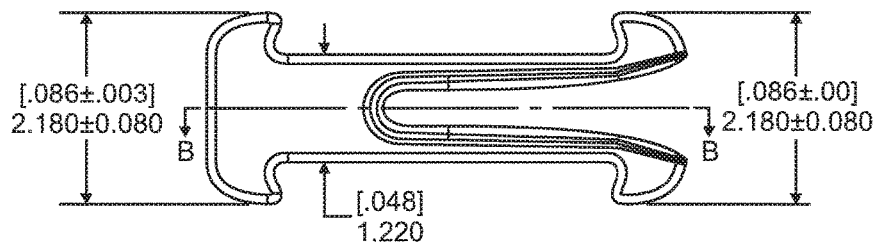
Figure 5G:
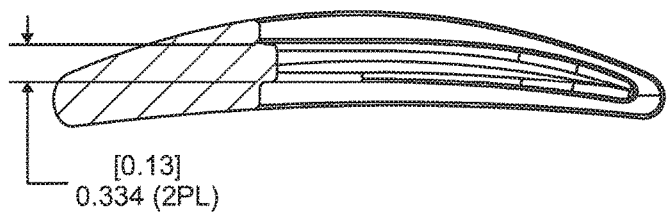

The prosthesis 500 could have the dimensions shown in FIGS. 5B through 5G. These dimensions are for illustration only. In these figures, the dimensions are expressed as numbers in brackets (representing dimensions in inches) over numbers without brackets (representing dimensions in millimeters). Dimensions associated with a radius of curvature are preceded by the letter "R" (such as in "R6.168"). In addition, the diagram shown in FIG. 5E represents the cross-section of the prosthesis 500 along line A-A in FIG. 5D, and the diagram shown in FIG. 5G represents the cross-section of the prosthesis 500 along line B-B in FIG. 5F. As shown in FIG. 5G, the prosthesis 500 could (but need not) be hollow within the undivided portion of the prosthesis 500 near the end 502 and may or may not be filled with a liquid, gel, or other material.

As explained in more detail below, an insert can be placed between or around the multiple portions 506a-506b of the end 504 of the prosthesis 500. The insert can be permanently or removably placed between or around the portions 506a-506b of the end 504 of the prosthesis 500. For example, the insert could be placed between or around the portions 506a-506b of the end 504 after the prosthesis 500 has been implanted in a scleral tunnel in a patient's eye. The insert could later be removed, such as to facilitate removal of the prosthesis 500 from the scleral tunnel.

The insert may generally help to stabilize the prosthesis 500 (in addition to the stabilization already provided by the wider ends). For example, the insert could help to prevent the portions 506a-506b of the prosthesis 500 from separating excessively, which could pull the opposite end 502 through the scleral tunnel and force the prosthesis 500 out of the tunnel completely. The insert could also function to reduce or prevent rotation of the prosthesis 500 within the scleral tunnel. For instance, the insert may help to ensure that the end 504 of the prosthesis 500 maintains a desired width and therefore remains wide enough to prevent the prosthesis 500 from rolling over once implanted in the scleral tunnel. Moreover, the insert can be inserted into or around the prosthesis 500 only after the prosthesis 500 has been implanted, which enables the portions 506a-506b of the prosthesis 500 to be pushed together during implantation but prevents portions 506a- 506b from coming together after implantation (reducing the likelihood that the prosthesis 500 can exit the scleral tunnel).

FIGS. 6A through 6G illustrate a sixth example scleral prosthesis 600 in accordance with this disclosure. The embodiment of the scleral prosthesis 600 shown in FIGS. 6A through 6G is for illustration only. Other embodiments of the scleral prosthesis 600 could be used without departing from the scope of this disclosure.

Figure 6A:
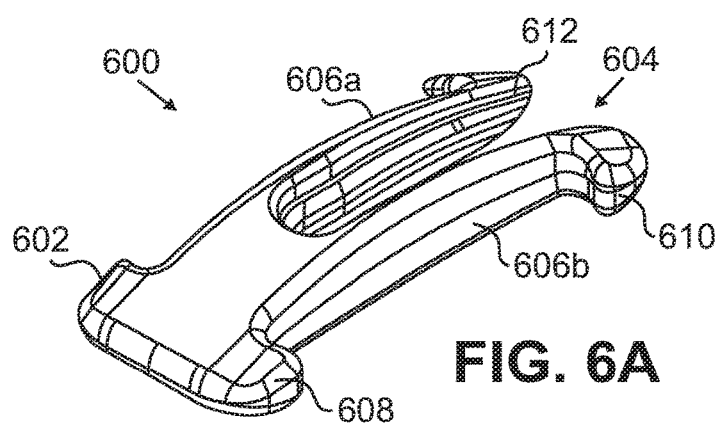
FIGS. 6A through 6G illustrate a sixth example scleral prosthesis in accordance with this disclosure.
Figure 6B:
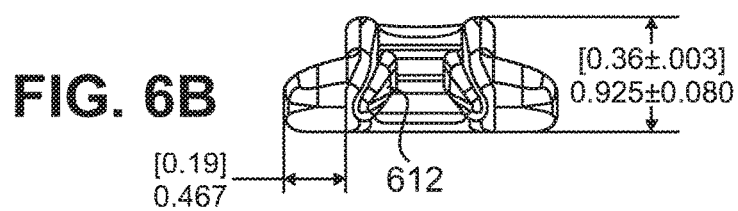
Figure 6C:
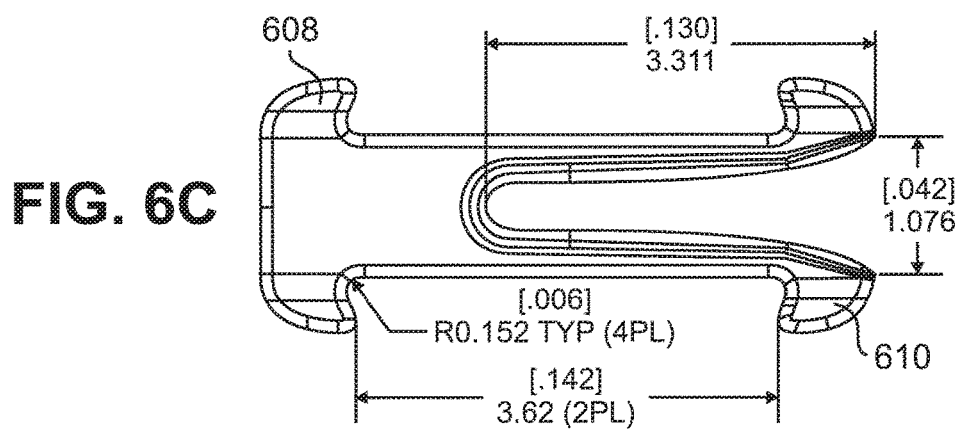
Figure 6D:
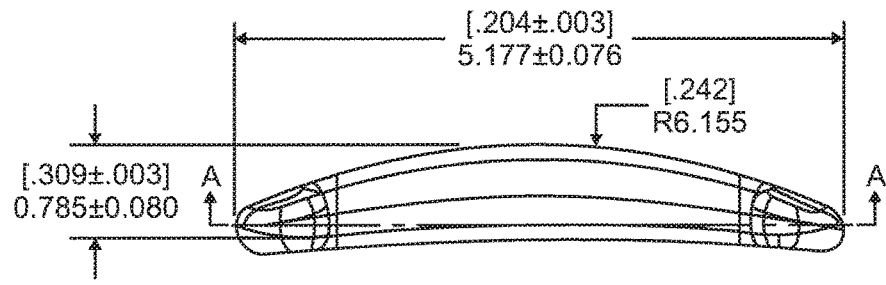

As shown in FIG. 6A, the scleral prosthesis 600 has two opposing ends 602-604. In this example, again only one end 604 of the prosthesis 600 is split or divided into multiple portions 606a-606b (although both ends could be divided). As shown FIG. 6B, the prosthesis 600 generally has a more rectangular cross-section, where the bottom surfaces of the ends 602-604 are flatter than in the prosthesis 500.

As shown here, portions 608-610 of the ends 602-604 of the prosthesis 600 are hook-shaped, and the prosthesis 600 includes ridges 612 along the inner sides of the portions 606a-606b. The ridges 612 generally travel lengthwise along the portions 606a-606b of the prosthesis 600 and may or may not be linked along the curved intersection of the portions 606a-606b. Again, the ends 602-604 of the prosthesis 600 are wider than the middle, helping to stabilize the prosthesis 600.

Figure 6E:
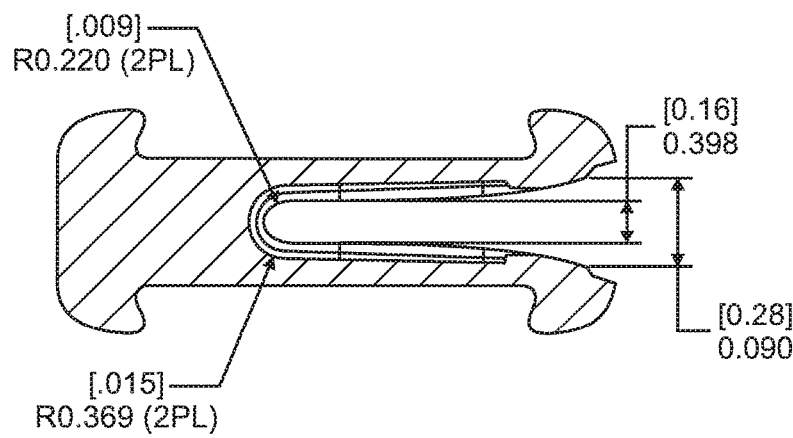
Figure 6F:
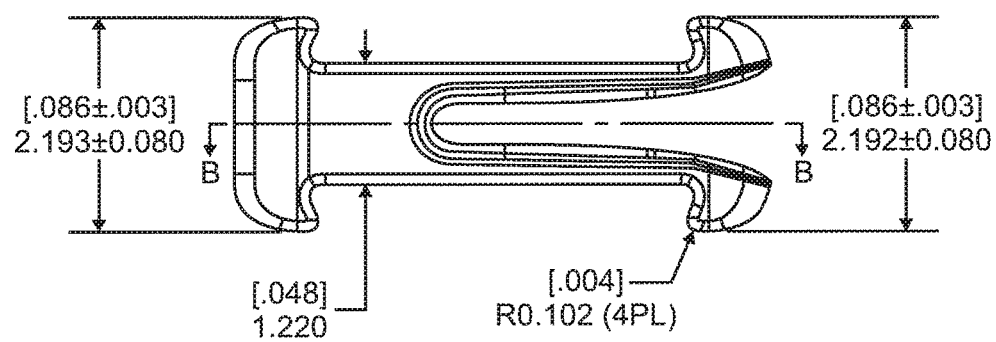
Figure 6G:
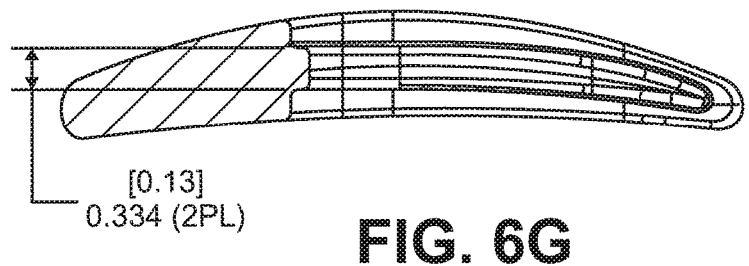

The prosthesis 600 could have the dimensions shown in FIGS. 6B through 6G. These dimensions are for illustration only. In these figures, the dimensions are again expressed as numbers in brackets (representing inches) over numbers without brackets (representing millimeters), and dimensions associated with a radius of curvature are preceded by the letter "R." In addition, the diagram shown n FIG. 6E represents the cross-section of the prosthesis 600 along line A-A in FIG. 6D, and the diagram shown in FIG. 6G represents the cross-section of the prosthesis 600 along line B-B in FIG. 6F. Again, the prosthesis 600 may or may not be hollow within the undivided portion of the prosthesis 600 near the end 602 and may or may not be filled with a liquid, gel, or other material.

As shown below, the prosthesis 600 can include an insert permanently or removably placed between or around the multiple portions 606a-606b of the end 604 of the prosthesis 600. The insert may generally help to stabilize the prosthesis 600 (in addition to the stabilization already provided by the wider ends).

FIGS. 7A through 7G illustrate a seventh example scleral prosthesis 700 in accordance with this disclosure. The embodiment of the scleral prosthesis 700 shown in FIGS. 7A through 7G is for illustration only. Other embodiments of the scleral prosthesis 700 could be used without departing from the scope of this disclosure.

Figure 7A:
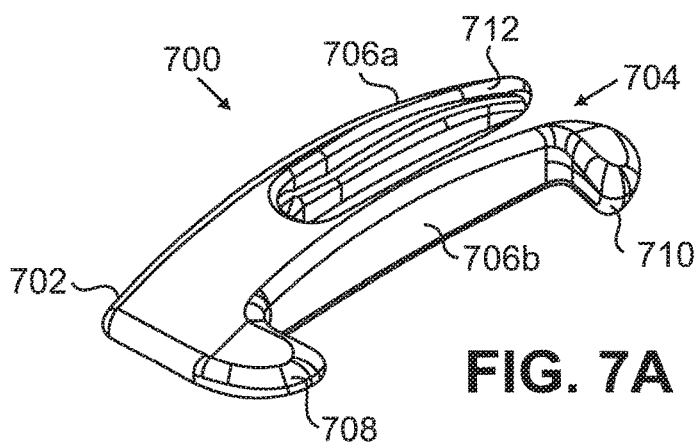
FIGS. 7A through 7G illustrate a seventh example scleral prosthesis in accordance with this disclosure.
Figure 7B:
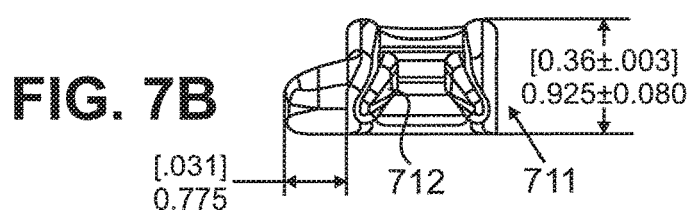
Figure 7C:
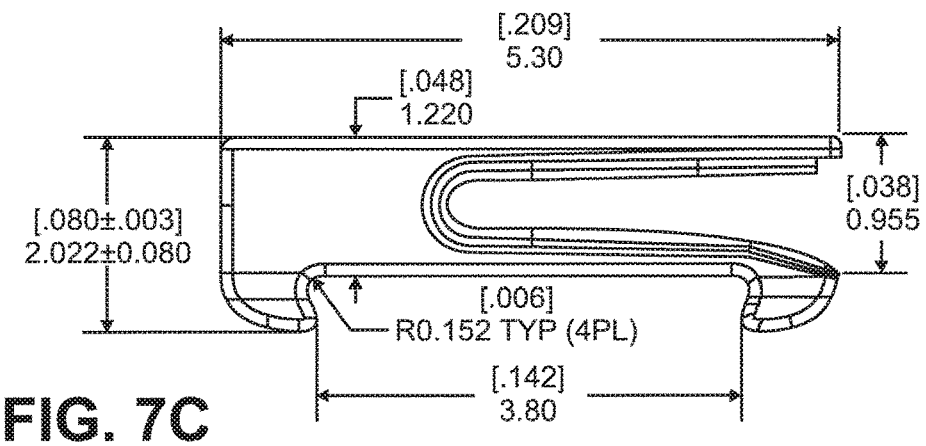
Figure 7D:
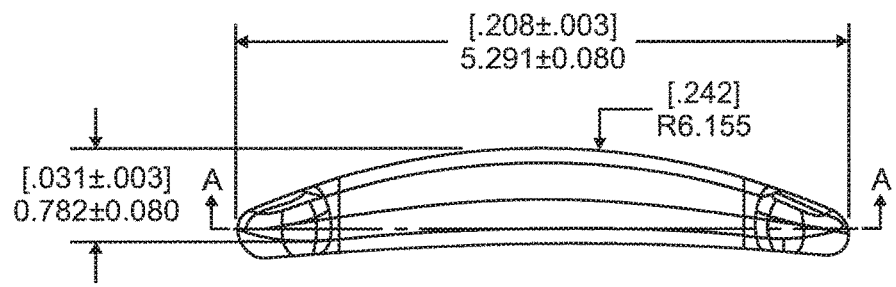

As shown in FIG. 7A, the scleral prosthesis 700 has two opposing ends 702-704. Once again, in this example, only one end 704 of the prosthesis 700 is split or divided into multiple portions 706a-706b (although both could be). As opposed to prior prostheses, as shown in FIG. 7B, the prosthesis 700 does not have a symmetrical cross-section. Instead, the prosthesis 700 has one side 711 that is relatively flat along the entire length of the prosthesis 700. Here, the ends 702-704 have sides that are aligned with each other along the side 711 of the prosthesis 700. Also, each of the ends 702-704 includes a single portion 708-710, respectively, that is hook-shaped. As a result, both ends 702-704 are still wider than the middle portion of the prosthesis 700 and help stabilize the prosthesis 700, but the ends 702-704 may not be as wide as prior prostheses.

As with the prostheses 500 and 600, the prosthesis 700 includes ridges 712 along the inner sides of the portions 706a-706b. The ridges 712 generally travel lengthwise along the portions 706a-706b of the prosthesis 700 and may or may not be linked together.

Figure 7E:
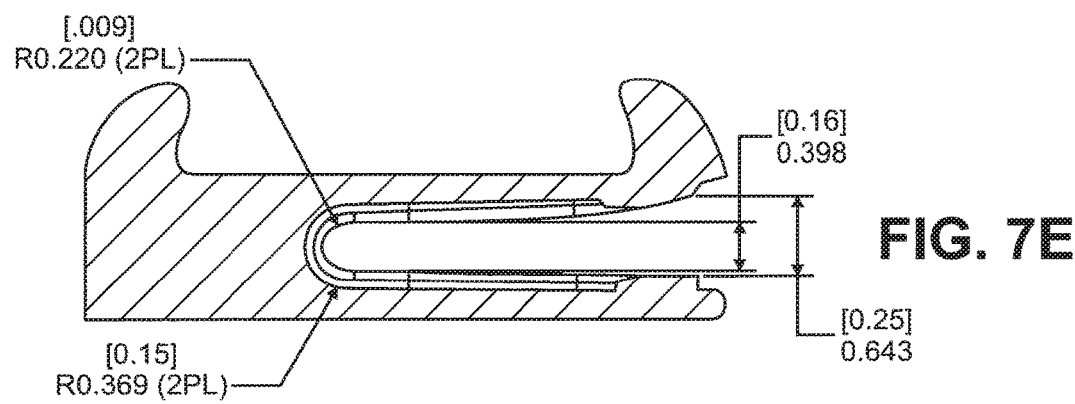
Figure 7F:
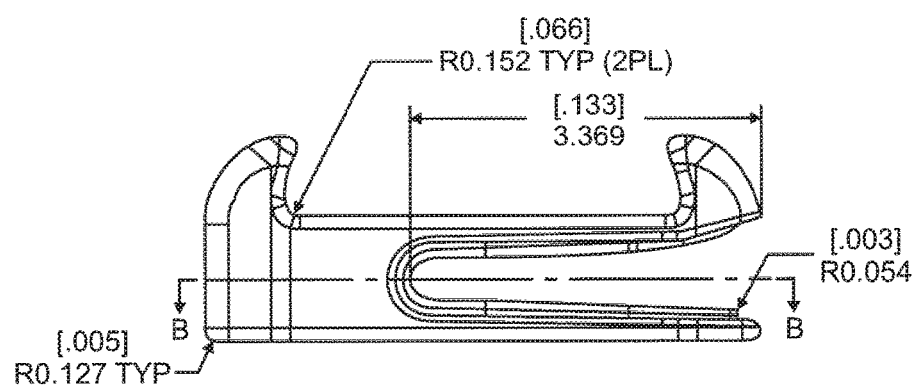
Figure 7G:
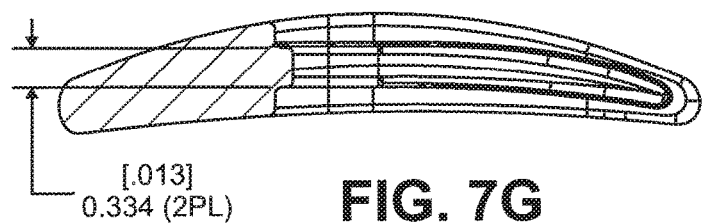

The prosthesis 700 could have the dimensions shown in FIGS. 7B through 7G. These dimensions are for illustration only. The diagram shown in FIG. 7E represents the cross-section of the prosthesis 700 along line A-A in FIG. 7D, and the diagram shown in FIG. 7G represents the cross-section of the prosthesis 700 along line B-B in FIG. 7F. Also, the prosthesis 700 may or may not be hollow within the undivided portion of the prosthesis 700 near the end 702 and may or may not be filled with a liquid, gel, or other material. As explained below, the prosthesis 700 may include an insert permanently or removably placed between or around the multiple portions 706a-706b of the end 704 of the prosthesis 700. The insert may generally help to stabilize the prosthesis 700 (in addition to the stabilization already provided by the wider ends).

Although FIGS. 1A through 7G illustrate various examples of scleral prostheses, various changes may be made to FIGS. 1A through 7G. For example, the sizes, shapes, and dimensions of the features of the scleral prostheses are for illustration only and can be altered in any suitable manner. Also, various features shown and described with respect to one of the scleral prostheses could be used with other scleral prostheses. As a particular example, the insert 408 of the prosthesis 400 could be used with any other suitable scleral prosthesis. As another particular example, a difference between the prostheses shown in FIGS. 3A-3F and the prostheses shown in FIGS. 5A-7G is that (when looking from an end viewpoint) the top edges of the ends have been shaved in FIGS. 5A-7G so that they slope downwards from top to bottom at about a 45° angle. This same feature could be used with any other prosthesis.

FIGS. 8A through 8F illustrate an example insertion of a scleral prosthesis into a patient's eye in accordance with this disclosure. The example insertion of the scleral prosthesis shown in FIGS. 8A through 8F is for illustration only. Other techniques could be used to insert a scleral prosthesis into a patient's eye without departing from the scope of this disclosure.

Figure 8A:
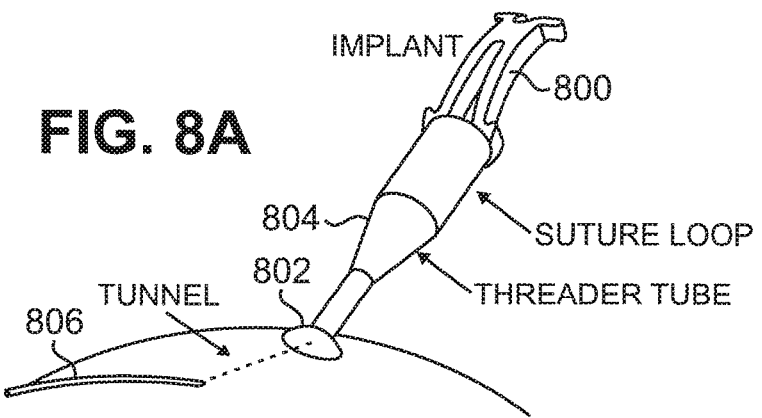
FIGS. 8A through 8F illustrate an example insertion of a scleral prosthesis into a patient's eye in accordance with this disclosure.

As shown in FIG. 8A, a prosthesis 800 is being implanted into a scleral tunnel 802 in a patient's eye. The prosthesis 800 could represent any suitable prosthesis, such as one of the prostheses discussed above or any other suitable prosthesis. In this example, the prosthesis 800 is inserted into a threader tube 804, which is used to compress or push together the split or divided portions of the prosthesis 800 for insertion into the scleral tunnel 802. The prosthesis 800 is pulled into the scleral tunnel 802 by the threader tube 804 and, optionally, a suture 806 that has been threaded through the scleral tunnel 802. The end of the suture 806 in this example includes two loops that are placed through the threader tube 804 and connected to one end of the prosthesis 800. In this example, the loops of the suture 806 loop around the cylindrical or triangular areas at one end of the prosthesis 800.

Figure 8B:
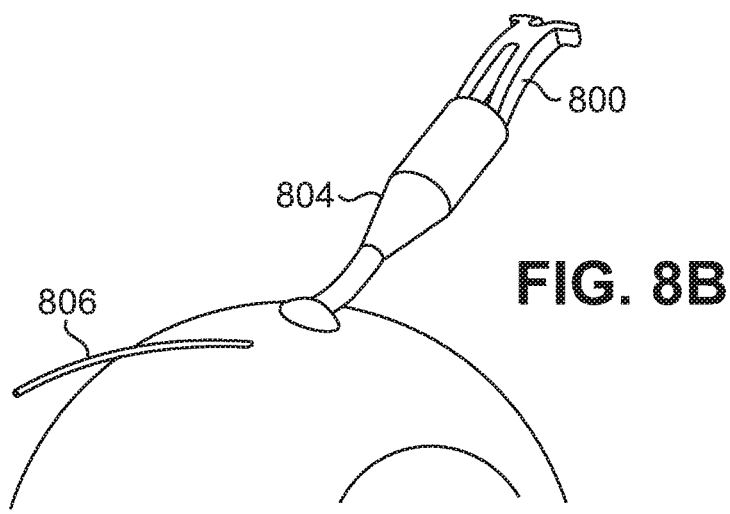
Figure 8C:
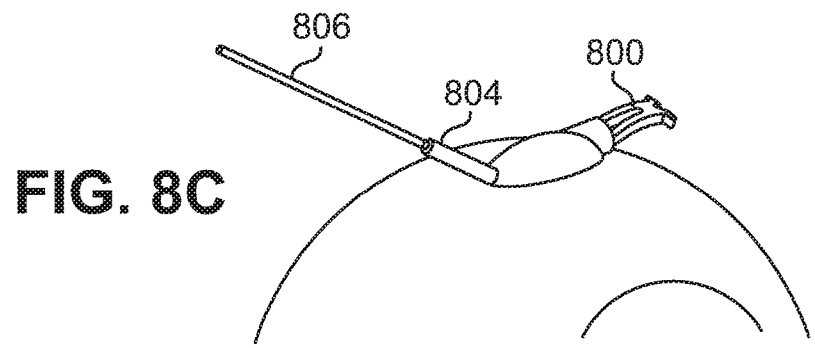
Figure 8D:
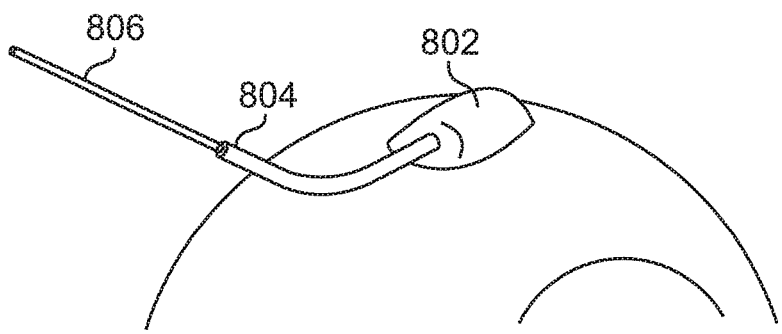
Figure 8E:
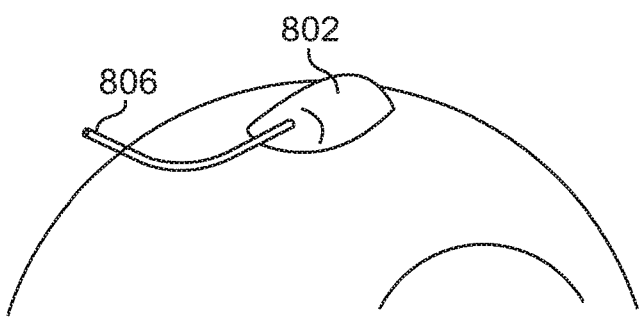
Figure 8F:
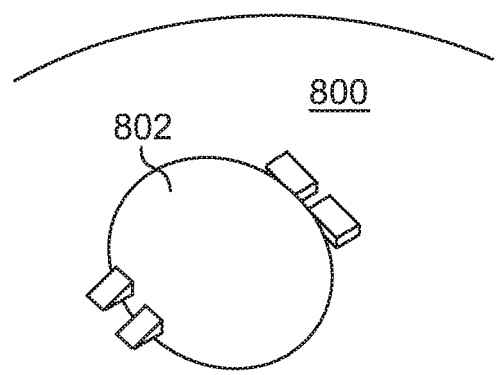

As shown in FIGS. 8A and 8B, one end of the prosthesis 800 is connected to the suture 806 and can be inserted into the threader tube 804. As shown in FIGS. 8C and 8D, the threader tube 804 and the suture 806 can then be pulled so that the prosthesis 800 is pulled into the scleral tunnel 802. In some embodiments, the prosthesis 800 is both pulled into the scleral tunnel 802 (such as by using the threader tube 804 and/or the suture 806) and pushed into the scleral tunnel 802 (such as by using an instrument held by a surgeon). As shown in FIG. 8E, once the prosthesis 800 is implanted within the scleral tunnel 802, the threader tube 804 can be pulled off the prosthesis 800, and the suture 806 can be removed from the prosthesis 800. This leaves the prosthesis 800 in the scleral tunnel 802 as shown in FIG. 8F.

Although FIGS. 8A through 8F illustrate one example of an insertion of a scleral prosthesis into a patient's eye, various changes may be made to FIGS. 8A through 8F. For example, the threader tube 804 could have any suitable size or shape. Also, the suture 806 could be attached or coupled to the prosthesis 800 in any suitable manner. In addition, the suture 806 need not be used with the threader tube 804 to implant the prosthesis 800. In particular embodiments, the prosthesis 800 could be pulled into the scleral tunnel 802 using only the threader tube 804.

Figure 9A:
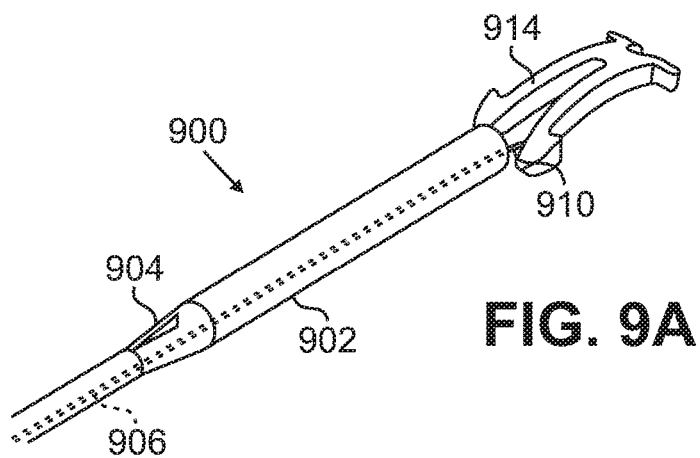
FIGS. 9A through 9C illustrate an example threader tube used to insert a scleral prosthesis into a patient's eye in accordance with this disclosure.
Figure 9B:
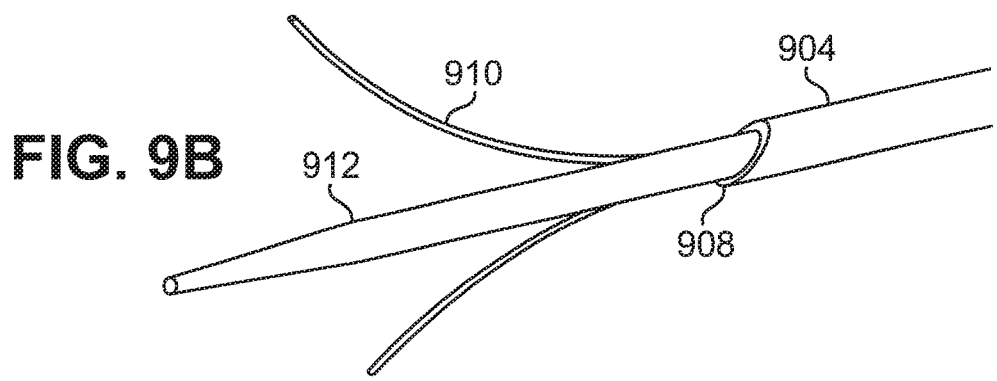
Figure 9C:
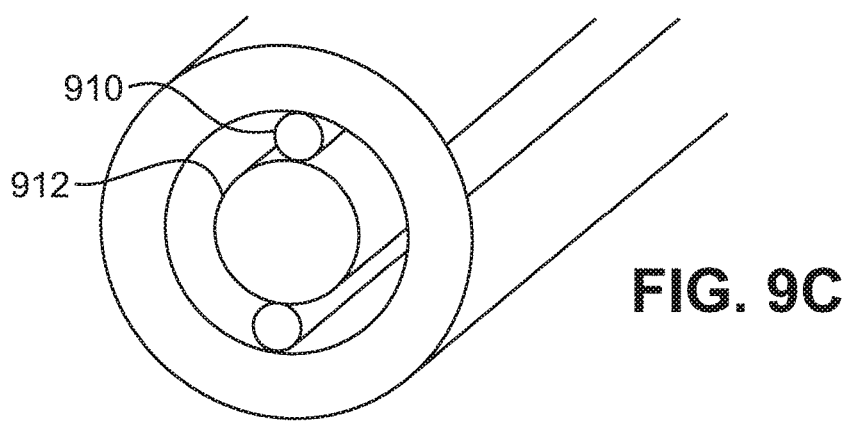

FIGS. 9A through 9C illustrate an example threader tube 900 used to insert a scleral prosthesis into a patient's eye in accordance with this disclosure. The embodiment of the threader tube 900 shown in FIGS. 9A through 9C is for illustration only. Other embodiments of the threader tube 900 could be used without departing from the scope of this disclosure.

In this example, the threader tube 900 includes a wider upper portion 902, a tapered portion 904, and a narrower lower portion 906. The lower portion 906 in this example includes an angled end 908. The threader tube 900 could be formed from any suitable material(s), such as heat-shrink tubing formed from TEFLON PTFE (polytetrafluoroethylene). Also, the threader tube 900 could have any suitable shape that allows the threader tube 900 to be pulled through a scleral tunnel. For example, the threader tube 900 could have an overall length of 3.0 cm (±0.5 cm). The upper portion 902 could have a length of 1.0 cm (±0.2 cm), an internal diameter of 1.0 mm, and a minimum wall thickness of 0.08 mm. The lower portion 906 could have an internal diameter of 0.5 mm and a recovered minimum wall thickness of 0.12 mm. In addition, the end 908 of the lower portion 906 could have an angle of 30°.

Optionally, a suture 910 can be placed through the threader tube 900, and a rod 912 can be inserted into the lower portion 906 of the threader tube 900. The illustration in FIG. 9C represents the cross-section of the threader tube 900 along the lower portion 906 of the threader tube 900. The suture 910 travels through the threader tube 900, loops around a scleral prosthesis 914, and returns through the threader tube 900. The suture 910 in this example loops around the central body of the prosthesis 914 (as opposed to looping over portions of the closer end of the prosthesis as shown in FIGS. 8A through 8F). The suture 910 represents any suitable suture made of any suitable material(s), such as 6-0 NYLON or PROLENE sutures having a 0.1 mm diameter.

The rod 912 in this example includes a tapered and rounded end that can be inserted through a scleral tunnel ahead of the lower portion 906 of the threader tube 900. The rod 912 can be used to facilitate insertion of the threader tube 900 into a scleral tunnel of a patient's eye. For example, the rod 912 may help the scleral tunnel to open and obtain a larger size before the lower portion 906 of the threader tube 900 is inserted into the scleral tunnel. The rod 912 could be formed from any suitable material(s) and can have any suitable size or shape, such as a cigar-shaped rod having a maximum diameter of 0.3 mm. Also, both ends of the rod 912 could, but need not, have the shape shown in FIG. 9B.

Although FIGS. 9A through 9C illustrate one example of a threader tube 900 used to insert a scleral prosthesis into a patient's eye, various changes may be made to FIGS. 9A through 9C. For example, the threader tube 900 and rod 912 could have any suitable size or shape. Also, the suture 910 need not loop around the central body of the prosthesis 914 and could loop around or be attached to or associated with the prosthesis 914 in any suitable manner, such as by being looped around the closer end of the prosthesis 914. Further, the suture 910 and/or the rod 912. need not be used along with the threader tube 900 to insert a scleral prosthesis into a scleral tunnel.

Figure 10A:
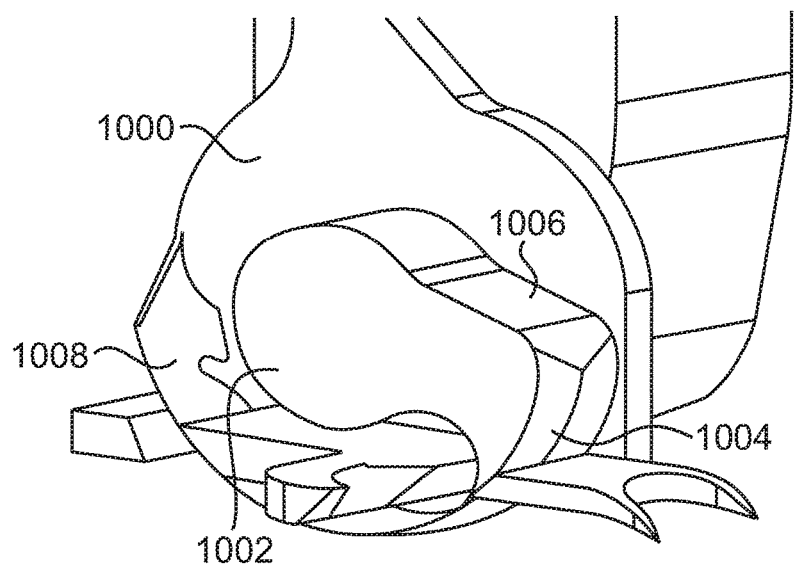
FIGS. 10A and 10B illustrate an example surgical blade used to create a scleral tunnel for receiving a scleral prosthesis in accordance with this disclosure.
Figure 10B:
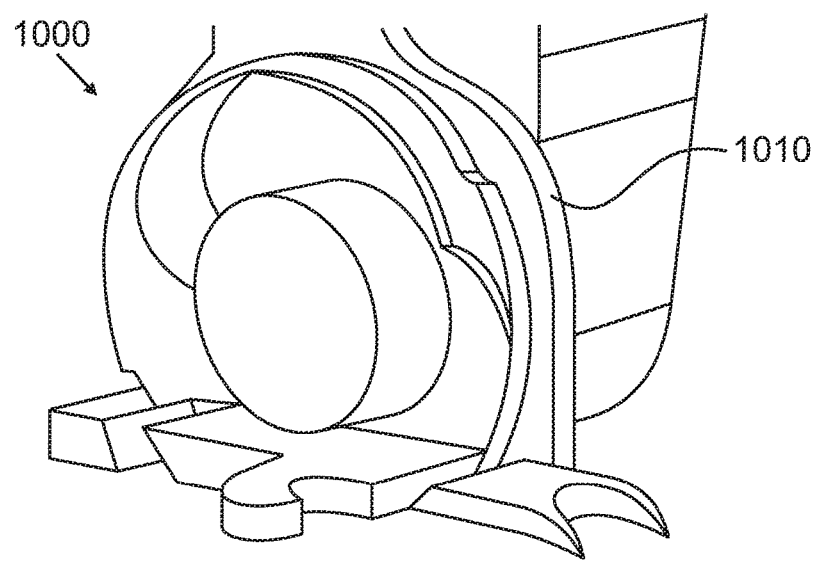

FIGS. 10A and 10B illustrate an example surgical blade 1000 used to create a scleral tunnel for receiving a scleral prosthesis in accordance with this disclosure. The embodiment of the surgical blade 1000 shown in FIGS. 10A and 10B is for illustration only. Other embodiments of the surgical blade 1000 could be used without departing from the scope of this disclosure.

In this example, the surgical blade 1000 is used to automatically feed a suture through a scleral tunnel. The suture could then be used to pull a prosthesis into the scleral tunnel, such as is shown in FIGS. 8A through 8F and 9A through 9C. However, as noted above, the use of a suture to pull a prosthesis into a scleral tunnel is not required, and the surgical blade 1000 could be modified to simply form a scleral tunnel without pulling a suture through the tunnel.

As shown in FIGS. 10A and 10B, the surgical blade 1000 includes a central portion 1002, a curved cutting blade 1004, and a connecting segment 1006. The central portion 1002 is connected to a surgical tool and can be rotated in multiple directions to move the cutting blade 1004 into and out of the scleral tissue of a patient's eye. The connecting segment 1006 couples the central portion 1002 to the cutting blade 1004, helping to translate rotation of the central portion 1002 into movement of the cutting blade 1004.

In this example, the cutting blade 1004 includes a notch 1008. After the cutting blade 1004 is rotated into the scleral tissue of a patient's eye (and before it is rotated out of the scleral tissue), a suture 1010 can be placed in the notch 1008. In some embodiments, the suture 1010 could have multiple loops at its end, and the loops may be placed in the notch 1008. In other embodiments, the suture 1010 itself is placed within the notch 1008. The suture 1010 could be loaded into the notch 1008 in any suitable manner, such as automatically or manually. The cutting blade 1004 is then rotated out of the patient's scleral tissue, pulling the suture 1010 with it. This allows the suture 1010 to be pulled through the scleral tunnel in a patient's eye at the time that the scleral tunnel is formed. The suture 1010 also helps to mark the location of the scleral tunnel, allowing a surgeon or other personnel to quickly locate the scleral tunnel in the patient's eye after the surgical blade 1000 is removed.

Although FIGS. 10A and 10B illustrate one example of a surgical blade 1000 used to create a scleral tunnel for receiving a scleral prosthesis, various changes may be made to FIGS. 10A and 10B. For example, the surgical blade 1000 need not include a notch 1008, and the suture 1010 could be inserted through a scleral tunnel after the tunnel is formed. Also, as noted above, the suture 1010 could be omitted from the surgical procedure.

FIGS. 11A through 11D illustrate an eighth example scleral prosthesis 1100 in accordance with this disclosure. The embodiment of the scleral prosthesis 1100 shown in FIGS. 11A through 11D is for illustration only. Other embodiments of the scleral prosthesis 1100 could be used without departing from the scope of this disclosure.

In this example, the scleral prosthesis 1100 changes shape after being implanted into a scleral tunnel. For example, the prosthesis 1100 could be formed from a shape-memory metal or other material that changes shape when exposed to certain temperatures or temperature ranges, such as a nickel titanium alloy or Nitinol. In this example, the prosthesis 1100 before implantation may have the shape shown in FIG. 11A. Here, the prosthesis 1100 includes a generally flat central portion 1102 and two generally flat end portions 1104-1106. Each of the end portions 1104-1106 includes two separated sections 1108, which in this example are angled towards one another.

Figure 11A:
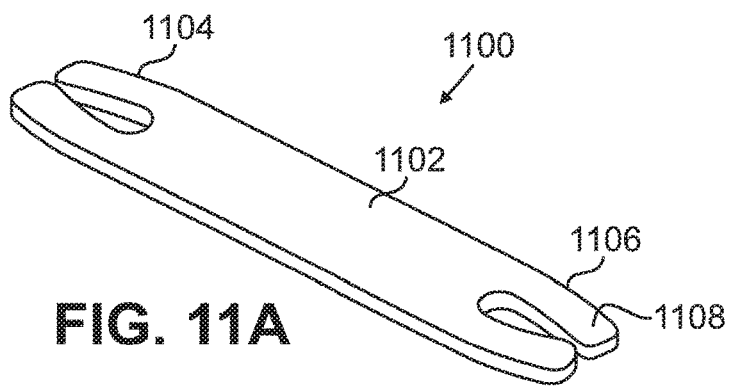
FIGS. 11A through 11D illustrate an eighth example scleral prosthesis in accordance with this disclosure.
Figure 11B:
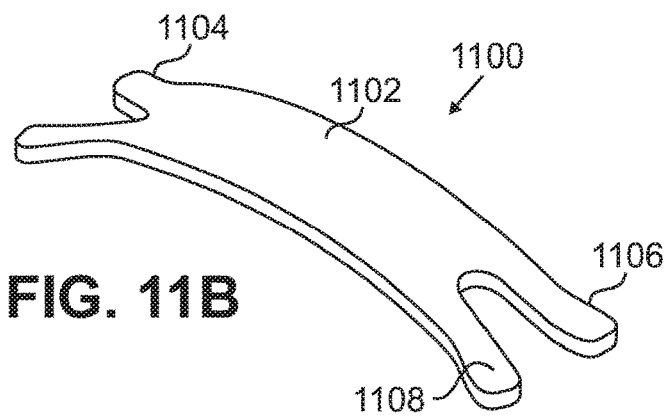

Once inserted into a scleral tunnel, the temperature of the patient's scleral tissue may cause the prosthesis 1100 to assume the shape shown in FIG. 11B. The central portion 1102 of the prosthesis 1100 is now arched or curved, and the sections 1108 of each end portion 1104-1106 angle away from one other. Also, the end portions 1104-1106 may be generally curved, while the tips of the end portions 1104-1106 are flatter to form splayed feet that provide support for the prosthesis 1100.

The prosthesis 1100 could be implanted into a patient's eye in any suitable manner. For example, the scleral prosthesis 1100 could be inserted into a scleral tunnel after a surgical blade has been used to form the scleral tunnel.

Figure 11C:
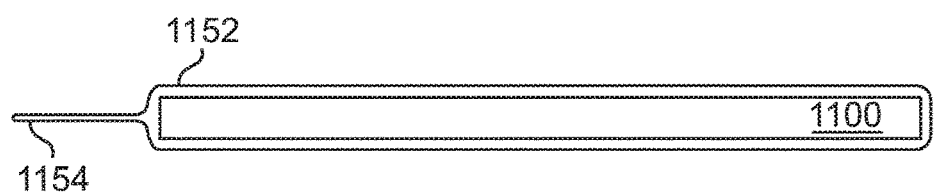
Figure 11D:
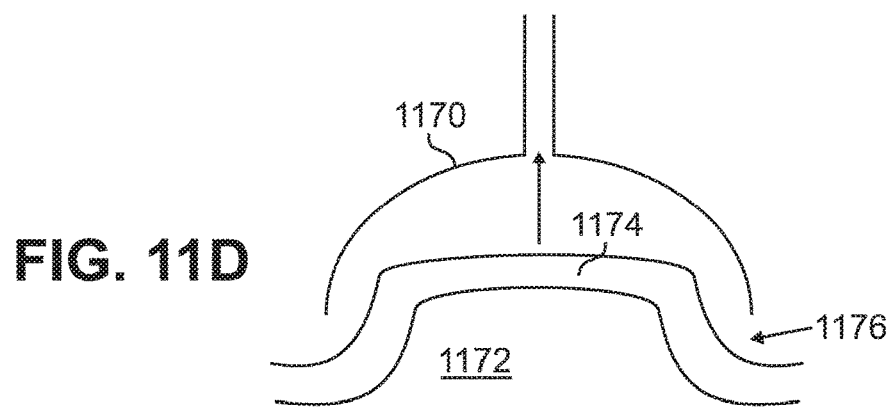

In other embodiments, as shown in FIG. 11C, the prosthesis 1100 could be placed within a sheath 1152 having an integrated blade 1154. The integrated blade 1154 can be used to form a scleral tunnel in a patient's eye while the prosthesis 1100 is being inserted into the scleral tissue. For example, as shown in FIG. 11D, a vacuum pot 1170 can be inserted onto a patient's eye, and vacuum forces could be used to pull up on the patient's scleral 1172 and conjunctiva 1174. At this point, an incision could be formed in the patient's eye, such as an incision at location 1176. This could include inserting the prosthesis 1100 into the patient's eye at the location 1176, using the blade 1154 to cut into and form an incision through the patient's eye at that location. By pulling on the patient's sclera 1172 before the incision is formed, a straight incision rather than a curved incision could be used to form a scleral tunnel. Although the incision is shown as occurring outside of the vacuum pot 1170, the vacuum pot 1170 could include a mechanism for forming an incision inside the vacuum pot 1170. Once implanted, the sheath 1152 could be opened and pulled through the scleral tunnel while the prosthesis 1100 is maintained in place (such as by a surgeon using a gripping tool to hold the prosthesis 1100 in place).

However, the prosthesis 1100 could be inserted in any other suitable manner, with or without using a sheathe, integrated blade, or vacuum pot.

In particular embodiments, the prosthesis 1100 may be malleable and caused to assume the shape shown in FIG. 11A at lower temperatures (in a "martensite" phase), such as temperatures below 60° F. At temperatures above 60° F. (in an "austenite" phase), the prosthesis 1100 may assume the arched shape shown in FIG. 11B. The flatter shape of the prosthesis 1100 shown in FIG. 11A may help to reduce the profile of the prosthesis 1100 during implantation, which may reduce the size of an incision needed in the scleral tissue of a patient's eye. As a particular example, the prosthesis 1100 in FIG. 11A could have an arched height of 250 microns, and the prosthesis 1100 in FIG. 11B could have an arched height of 900 microns. Also, because the prosthesis 1100 in FIG. 11A is generally flat, a straight incision could be used to form a scleral tunnel instead of a curved incision, reducing the complexity of forming the incision.

Although FIGS. 11A through 11D illustrate an eighth example scleral prosthesis 1100, various changes may be made to FIGS. 11A through 11D. For example, the prosthesis 1100 could have any suitable size or shape before and after implantation. As a particular example, while shown as including separated sections 1108 at its ends 1104-1106 in FIG. 11A, each end 1104-1106 of the prosthesis 1100 could be fully integrated, and each end 1104-1106 may branch into multiple sections 1108 only after implantation.

Figure 12A:
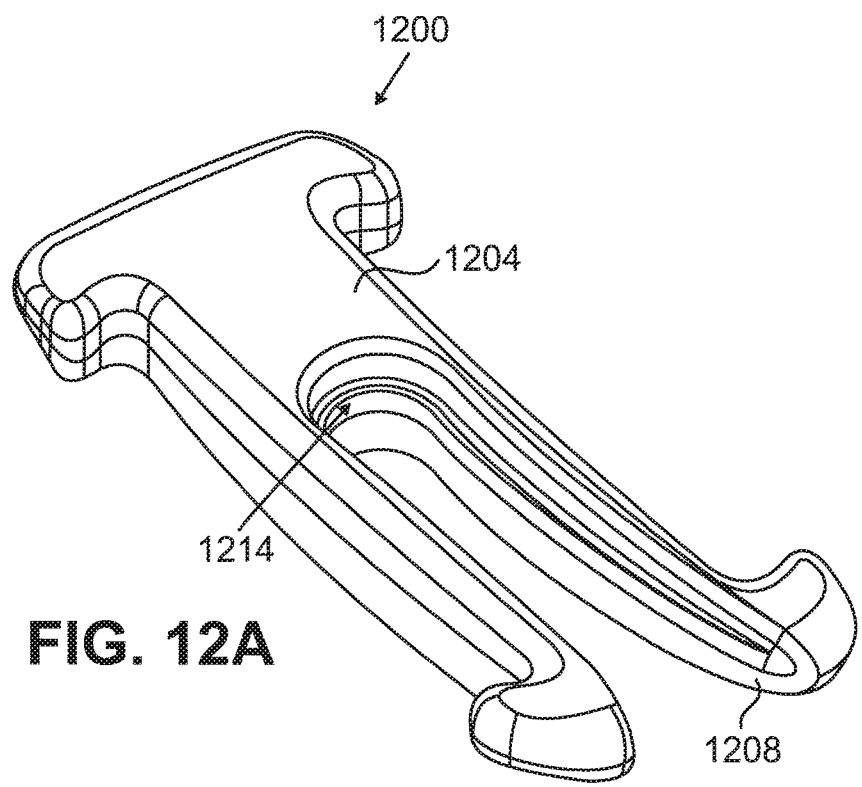
FIGS. 12A and 12B illustrate a ninth example scleral prosthesis in accordance with this disclosure.
Figure 12B:
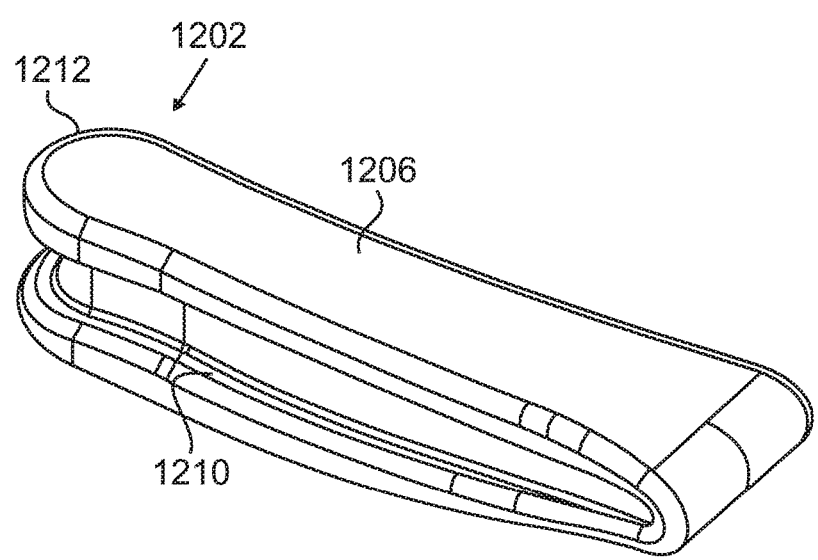

FIGS. 12A through 14B illustrate additional example prostheses having inserts placed between portions or "legs" of one end of each of these prostheses. FIGS. 12A and 12B illustrate a ninth example scleral prosthesis 1200 in accordance with this disclosure. The embodiment of the scleral prosthesis 1200 shown in FIGS. 12A and 12B is for illustration only. Other embodiments of the scleral prosthesis 1200 could be used without departing from the scope of this disclosure.

In this example, the scleral prosthesis 1200 is configured to receive an insert 1202. The prosthesis 1200 includes a textured bottom surface 1204, and the insert 1202 includes a textured bottom surface 1206 (although this feature could be omitted). Also, the interior sides of the legs of the prosthesis 1200 have "male" ridges 1208, and the insert 1202 has "female" slots 1210 that guide the insert 1202 smoothly between the legs of the prosthesis 1200 (after the prosthesis 1200 itself has been inserted in a scleral tunnel).

In addition, the insert 1202 includes a slightly wider circular "male" area 1212 at the interior end of the insert 1202, which can be inserted into a corresponding circular "female" expansion 1214 on the prosthesis 1200 itself. As the insert 1202 approaches the end of its travel into the prosthesis 1200, the area 1212 can be snapped into the expansion 1214, which helps to ensure that the insert 1202 does not fall out of the prosthesis 1200 after implantation.

The insert 1212 can be permanently or removably placed between the legs of the prosthesis 1200, For example, the insert 1212 could be placed between the legs of the prosthesis 1200 after the prosthesis 1200 has been implanted in a scleral tunnel in a patient's eye. The insert 1212 could later be removed, such as to facilitate removal of the prosthesis 1200 from the scleral tunnel.

The insert 1212 may generally help to stabilize the prosthesis 1200 (in addition to the stabilization already provided by its wider ends). For example, the insert 1212 could help to prevent the legs of the prosthesis 1200 from separating excessively, which could pull the opposite end through the scleral tunnel and force the prosthesis 1200 out of the tunnel completely. The insert 1212 could also function to reduce or prevent rotation of the prosthesis 1200 within the scleral tunnel. For instance, the insert 1212 may help to ensure that the legs of the prosthesis 1200 form an end having a desired width, so the end remains wide enough to prevent the prosthesis 1200 from rolling over once implanted in the scleral tunnel. Moreover, the insert 1212 can be inserted into or around the prosthesis 1200 only after the prosthesis 1200 has been implanted, which enables the legs of the prosthesis 1200 to be pushed together during implantation but prevents the legs from coming together after implantation.

FIGS. 13A through 13D illustrate a tenth example scleral prosthesis 1300, 1350 in accordance with this disclosure. The embodiments of the scleral prostheses 1300, 1350 shown in FIGS. 13A through 13D are for illustration only. Other embodiments of the scleral prostheses 1300, 1350 could be used without departing from the scope of this disclosure.

Figure 13A:
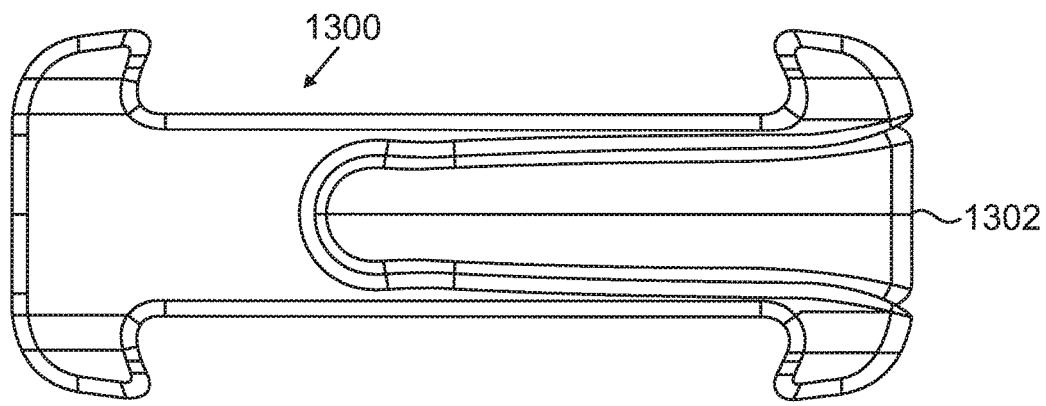
FIGS. 13A through 13D illustrate a tenth example scleral prosthesis in accordance with this disclosure.
Figure 13B:
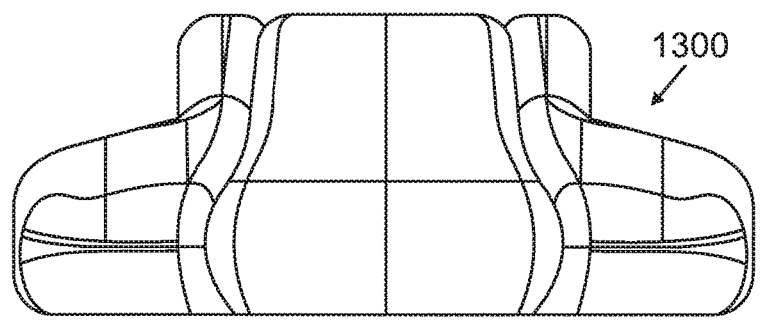
Figure 13C:
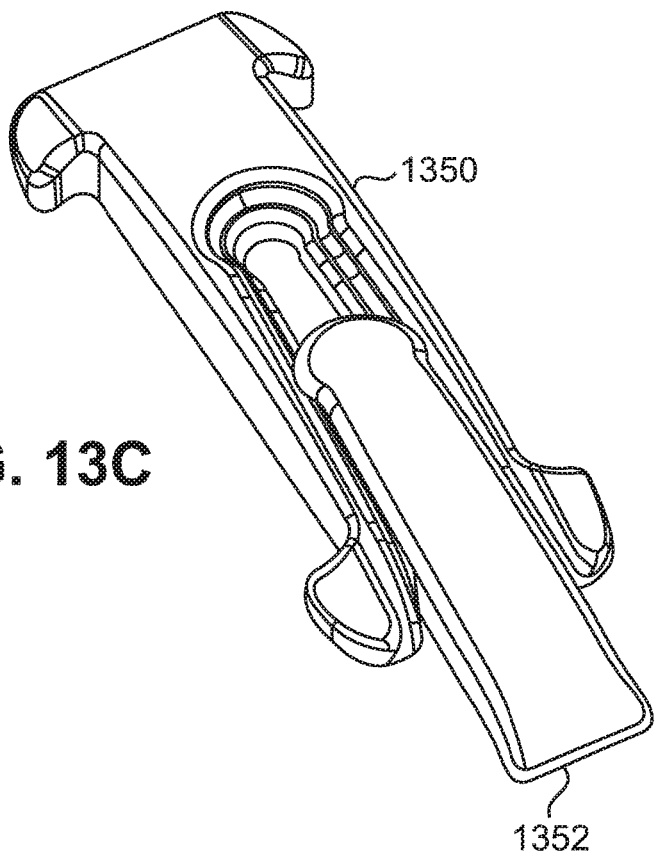
Figure 13D:
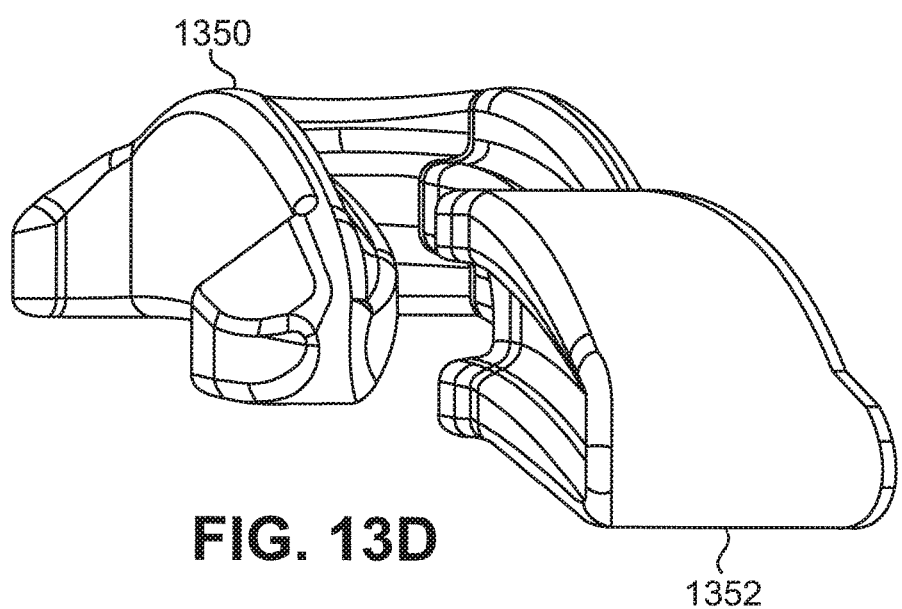

As shown in FIGS. 13A and 13B, an insert 1302 can be placed between the legs of the prosthesis 1300. Similarly, as shown in FIGS. 13C and 13D, an insert 1352 can be placed between the legs of the prosthesis 1350. The inserts 1302 and 1352 can function in the same or similar manner as the insert 1202 described above. Moreover, the same mechanisms (male ridges, female slots, male areas, and female expansions) could be used with the prostheses 1300, 1350 and inserts 1302, 1352.

Figure 14A:
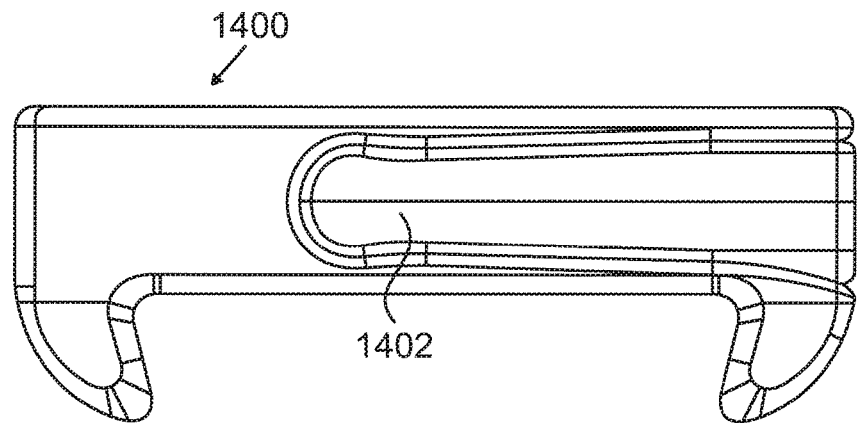
FIGS. 14A and 14B illustrate an eleventh example scleral prosthesis in accordance with this disclosure.
Figure 14B:
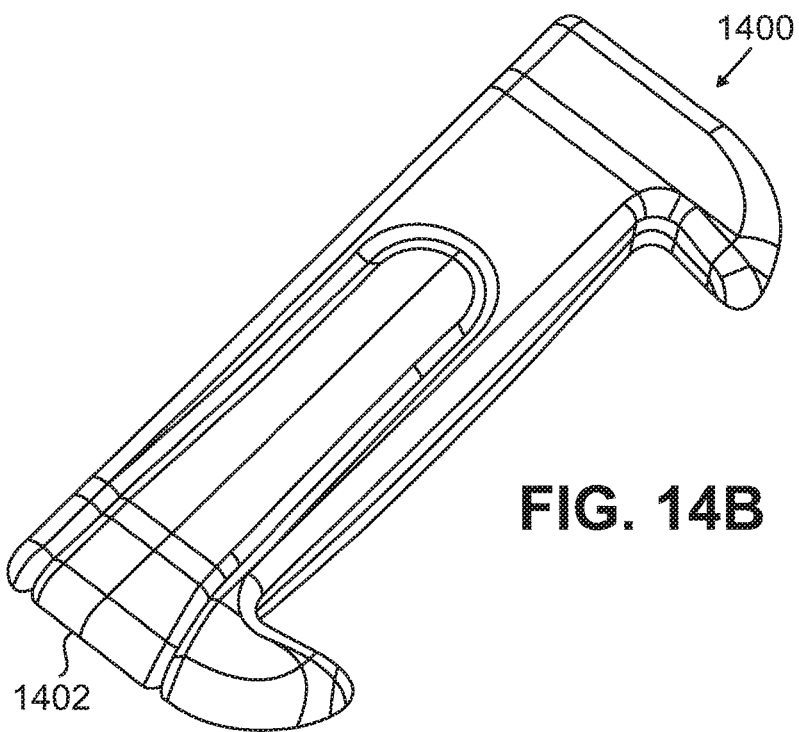

FIGS. 14A and 14B illustrate an eleventh example scleral prosthesis in accordance with this disclosure. The embodiment of the scleral prosthesis 1400 shown in FIGS. 14A and 14B is for illustration only. Other embodiments of the scleral prosthesis 1400 could be used without departing from the scope of this disclosure.

As shown in FIGS. 14A and 14B, an insert 1402 can be placed between the legs of the prosthesis 1400. The insert 1402 can function in the same or similar manner as the insert 1202 described above. Moreover, the same mechanisms (male ridges, female slots, male areas, and female expansions) could be used with the prosthesis 1400 and insert 1402.

In particular embodiments, the prostheses 1200-1400 shown in FIGS. 12A through 14B represents the same or similar prostheses described above in FIGS. 5A through 7G. However, the inserts could be used with any other suitable prosthesis.

Although FIGS. 12A through 14B illustrate various examples of scleral prostheses having inserts, various changes may be made to FIGS. 12A through 14B. For example, the sizes, shapes, and dimensions of the features of the scleral prostheses are for illustration only and can be altered in any suitable manner. Also, various features shown and described with respect to one of the scleral prostheses could be used with other scleral prostheses (including the prostheses shown in FIGS. 1 through 7G).

In addition, in some embodiments, any of the scleral prostheses described above could be fabricated using at least one magnetic material. For example, the entire body of a scleral prosthesis could be formed from at least one biocompatible magnetic material, or the scleral prosthesis could be formed from at least one non-biocompatible magnetic material and then encased in a biocompatible cover or shell. Also, a portion of a scleral prosthesis could be formed from at least one magnetic material. For instance, when a scleral prosthesis includes an insert (such as is shown in FIGS. 4A and 12A through 14B), the body or the insert could be formed from at least one magnetic material, or both the body and the insert could be formed from the same magnetic material(s) or from different magnetic materials. In some cases, the body and the insert could be magnetically attracted to each other in order to help secure the insert to the body. This could be accomplished using at least one magnetic material in the body and at least one metal in the insert (or vice versa). This could also be done using magnetic materials that are attracted to one another in the body and the insert.

Figure 15:
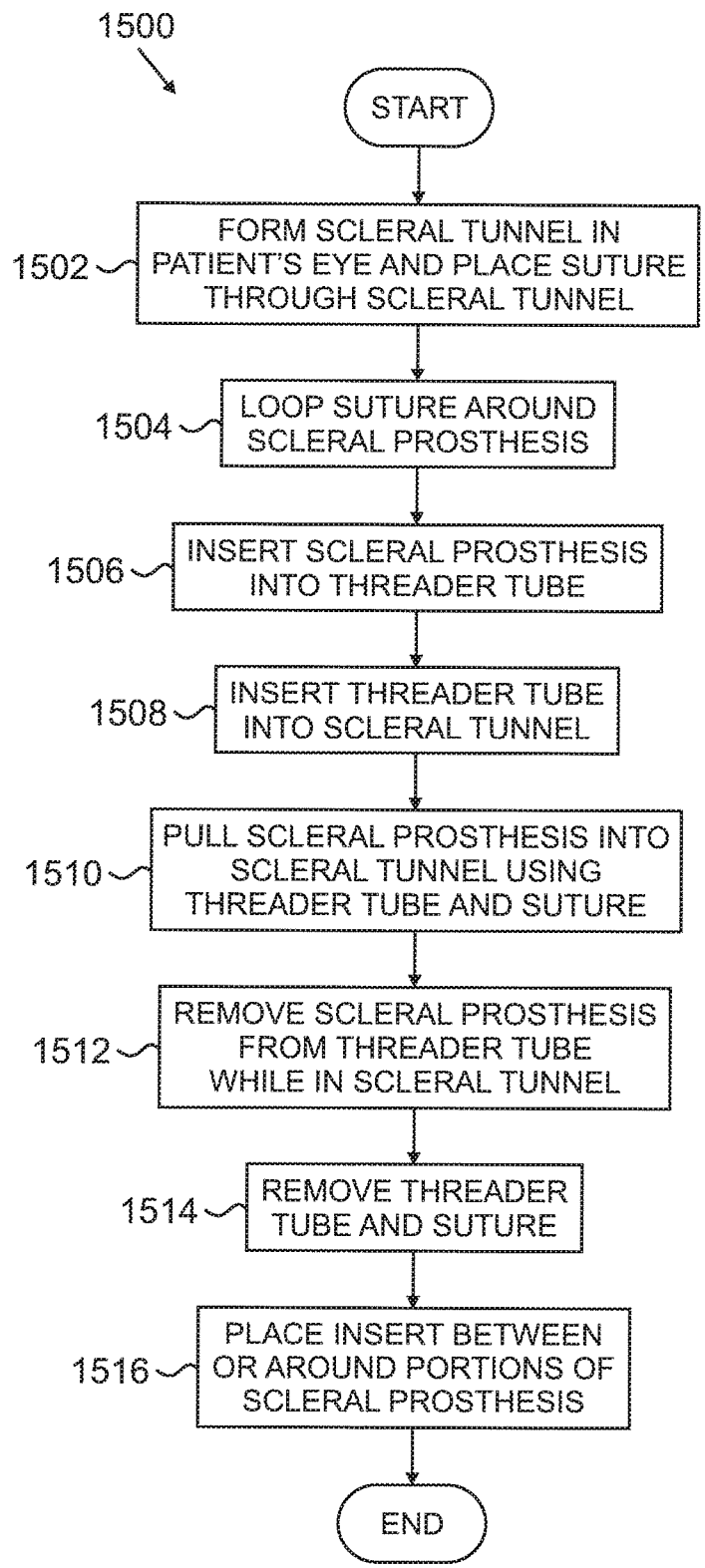
FIG. 15 illustrates an example method for inserting a scleral prosthesis into a patient's eye in accordance with this disclosure.

FIG. 15 illustrates an example method 1500 for inserting a scleral prosthesis into a patient's eye in accordance with this disclosure. The method 1500 shown in FIG. 15 is for illustration only. Other techniques could be used to insert a scleral prosthesis into a patient's eye without departing from the scope of this disclosure.

A scleral tunnel is formed in a patient's eye and a suture is placed through the scleral tunnel at step 1502. This could include, for example, using a tool with a curved cutting blade to form the scleral tunnel. This may also include pulling a suture through the scleral tunnel using the curved cutting blade. This may further include pulling a suture through the scleral tunnel after the curved cutting blade has completed the formation of the tunnel.

The suture is looped around a scleral prosthesis at step 1504. This could include, for example, placing loops at the end of a suture around one end of the scleral prosthesis (such as is done in FIGS. 8A through 8F). This could also include looping a suture around the central body portion of the scleral prosthesis (such as is done in FIGS. 9A through 9C). This step may also involve placing the suture through a threader tube.

The scleral prosthesis is inserted into the threader tube at step 1506. This could include, for example, inserting one end of the scleral prosthesis into the threader tube. Any suitable portion of the scleral prosthesis can be inserted into the threader tube, such as a portion that prevents premature ejection of the scleral prosthesis within the scleral tunnel.

The threader tube is inserted into the scleral tunnel at step 1508. This could include, for example, pushing the lower portion 906 of the threader tube into the scleral tunnel. This could also include pulling the threader tube into the scleral tunnel using the suture. This could further include using the rod 915 to open the scleral tunnel before the body of the threader tube is pulled into the scleral tunnel. The scleral prosthesis is pulled into the scleral tunnel at step 1510. This could include, for example, pulling the scleral prosthesis into its proper position within the scleral tunnel using the threader tube and the suture.

The scleral prosthesis is removed from the threader tube at step 1512, and the threader tube and the suture are removed at step 1514. This could include, for example, pulling the threader tube off the scleral prosthesis. This could also include pulling on one end of the suture to remove the suture from the scleral tunnel.

If necessary or desired, an insert can be placed between or around portions of the implanted scleral prosthesis at step 1516. This could include, for example, placing the insert between or around separated or divided portions of the scleral prosthesis to prevent rotation, flexing, ejection, or other movement by the scleral prosthesis.

Although FIG. 15 illustrates one example of a method 1500 for inserting a scleral prosthesis into a patient's eye, various changes may be made to FIG. 15. For example, any other suitable technique could be used to place a suture through the scleral tunnel. Also, any other suitable technique could be used to pull or push the scleral prosthesis into the scleral tunnel, including techniques omitting the use of a suture or rod.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A scleral prosthesis comprising:
an elongated body having a first free end and a second free end opposite the first free end, a maximum width of the body at each end wider than a maximum width of the body between the ends;
wherein the body comprises multiple first portions that form the first free end of the body and a part of the body between the ends, the first portions separated lengthwise along a substantial portion of a total length of the body;
wherein the first portions of the body are biased so that they maintain separation from one another without external interference but are configured to be pushed towards each other; and
wherein the body is configured to receive and retain, between the first portions of the body, an insert that is configured to maintain the separation of the first portions.

2. The scleral prosthesis of claim 1, wherein the first portions are separated along at least about half of the total length of the body.

3. The scleral prosthesis of claim 1, wherein the body further comprises multiple second portions that form the second free end of the body and another part of the body between the ends, the second portions separated lengthwise along the body.

4. The scleral prosthesis of claim 3, wherein:
the first portions run substantially parallel to one another along the body; and
the second portions run substantially parallel to one another along the body.

5. The scleral prosthesis of claim 3, wherein the second portions are separated along less than a quarter of the total length of the body.

6. The scleral prosthesis of claim 1, wherein each of the first portions includes a ridge extending inwardly from that first portion towards the other first portion of the body, the ridges configured to engage with slots of the insert.

7. The scleral prosthesis of claim 1, wherein the first portions meet at a point between the ends of the body and are not connected to each other between that point and the first free end of the body.

8. The scleral prosthesis of claim 1, wherein the body comprises at least one magnetic material.

9. A system comprising:
a scleral prosthesis configured to be implanted into scleral tissue of an eye, the scleral prosthesis comprising:
an elongated body having a first free end and a second free end opposite the first free end, a maximum width of the body at each end wider than a maximum width of the body between the ends;
wherein the body comprises multiple first portions that form the first free end of the body and a part of the body between the ends, the first portions separated lengthwise along a substantial portion of a total length of the body; and
wherein the first portions of the body are biased so that they maintain separation from one another without external interference but are configured to be pushed towards each other; and
an insert configured to be placed between the first portions of the body to maintain a separation of the first portions.

10. The system of claim 9, wherein the insert comprises a wider end portion that fits within a space proximate to a location where the first portions of the body meet.

11. The system of claim 9, wherein the first portions are separated along at least about half of the total length of the body.

12. The system of claim 9, wherein the body further comprises multiple second portions that form the second free end of the body and another part of the body between the ends, the second portions separated lengthwise along the body.

13. The system of claim 12, wherein:
the first portions run substantially parallel to one another along the body; and
the second portions run substantially parallel to one another along the body.

14. The system of claim 12, wherein the second portions are separated along less than a quarter of the total length of the body.

15. The system of claim 9, wherein each of the first portions includes a ridge extending inwardly from that first portion towards the other first portion of the body, the ridges configured to engage with slots of the insert.

16. The system of claim 9, wherein the first portions meet at a point between the ends of the body and are not connected to each other between that point and the first free end of the body.

17. The system of claim 9, wherein at least one of the body and the insert comprises at least one magnetic material.

18. A method comprising:
forming an elongated body of a scleral prosthesis, the body having a first free end and a second free end opposite the first free end, a maximum width of the body at each end wider than a maximum width of the body between the ends; and
forming an insert for the body;
wherein the body comprises multiple first portions that form the first free end of the body and a part of the body between the ends, the first portions separated lengthwise along a substantial portion of a total length of the body;
wherein the first portions of the body are biased so that they maintain separation from one another without external interference but are configured to be pushed towards each other; and
wherein the body is configured to receive and retain, between the first portions of the body, the insert to maintain the separation of the first portions.

19. The method of claim 18, wherein the first portions are separated along at least about half of the total length of the body.

20. The method of claim 18, wherein the first portions meet at a point between the ends of the body and are not connected to each other between that point and the first free end of the body.

* * * * *